(12) United States Patent
Hindsgaul et al.

(10) Patent No.: US 6,395,169 B1
(45) Date of Patent: May 28, 2002

(54) APPARATUS FOR SCREENING COMPOUND LIBRARIES

(75) Inventors: Ole Hindsgaul, Edmonton (CA); David C. Schriemer, 13619 109 Avenue, Edmonton, Alberta (CA), T5M 2G8

(73) Assignees: Ole Hindgual; David C. Schriemer, both of Alberta (CA)

( * ) Notice: Subject to any disclaimer, the term of this patent is extended or adjusted under 35 U.S.C. 154(b) by 0 days.

(21) Appl. No.: 09/412,319

(22) Filed: Oct. 5, 1999

Related U.S. Application Data

(62) Division of application No. 09/069,890, filed on Apr. 29, 1998, now Pat. No. 6,054,047.
(60) Provisional application No. 60/079,622, filed on Mar. 27, 1998.

(51) Int. Cl.[7] .............................................. B01D 15/08
(52) U.S. Cl. .................... 210/198.2; 210/656; 210/659; 210/143; 422/70
(58) Field of Search ................................ 210/635, 656, 210/659, 143, 198.2; 422/70; 436/161

(56) References Cited

U.S. PATENT DOCUMENTS

| | | | | |
|---|---|---|---|---|
| 4,842,701 A | | 6/1989 | Smith et al. ............. | 204/180.1 |
| 4,869,093 A | * | 9/1989 | Gilbert ....................... | 73/23.1 |
| 4,970,085 A | * | 11/1990 | Persson ................... | 426/330.5 |
| 5,106,756 A | * | 4/1992 | Zaromb ....................... | 436/161 |
| 5,481,476 A | * | 1/1996 | Windig ...................... | 364/498 |
| 5,503,805 A | * | 4/1996 | Sugarman .................. | 422/131 |
| 5,561,046 A | * | 10/1996 | Baxter ........................ | 435/7.1 |
| 5,646,046 A | * | 7/1997 | Fischer ........................ | 436/49 |
| 5,792,431 A | * | 8/1998 | Moore ....................... | 422/134 |
| 5,917,185 A | | 6/1999 | Carson et al. .............. | 250/288 |

FOREIGN PATENT DOCUMENTS

| | | | | |
|---|---|---|---|---|
| EP | 742 438 | 11/1996 | ................. | 210/656 |
| JP | 6-500396 | 6/1994 | ................. | 210/656 |
| JP | 06201650 A | 7/1994 | ................. | 210/656 |
| JP | 9-101306 | 9/1997 | ................. | 210/656 |
| JP | 10-500951 | 10/1998 | ................. | 210/656 |
| WO | WO 92/02815 | 2/1992 | ................. | 210/656 |
| WO | WO 95/25737 | 9/1995 | ................. | 210/656 |
| WO | WO 95/32425 | 11/1995 | ................. | 210/656 |
| WO | WO 96/32642 | 10/1996 | ................. | 210/656 |
| WO | WO 97/43301 | 11/1997 | ................. | 210/656 |
| WO | WO 97/43641 | 11/1997 | ................. | 210/656 |

OTHER PUBLICATIONS

Garr, The Use of Evaporative Light Scattering in Quality Control of Combinatorial Libraries, MDS Pan Labs, Inc. Apr. 28–29, 1997, pp. 1–18.*

Bean, K.A., *J Chromatogr B Biomed Sci Appl.*, 1997, 690, 65–75.

Calaf, R.E., et al., *Rapid Commun Mass Spectrom*, 1997, 11, 75–80.

Cornpropst, J.D., et al., *J. Chromatogr B Biomed Sci Appl.*, 1995, 673, 67–74.

(List continued on next page.)

*Primary Examiner*—Ernest G. Therkorn
(74) *Attorney, Agent, or Firm*—Burns, Doane, Swecker & Mathis LLP

(57) ABSTRACT

Disclosed are apparatus for screening compound libraries using frontal chromatography in combination with mass spectrometry to identify and rank those members of the library that bind to a target receptor. The apparatus of this invention also permit a compound library to be rapidly screened to determine if any member of the library has a higher affinity for the target receptor relative to a preselected indicator compound.

13 Claims, 7 Drawing Sheets

OTHER PUBLICATIONS

Chu, Y.-H., et al., *J. Am. Chem. Soc.* 1996, 118, 7827–7835.

Fang, L., et al., In *Proceedings of the 45th ASMS Conference on Mass Spectrometry and Allied Topics*, Palm Springs, CA, Jun. 1–5, 1997; p. 401.

Gaskell, S.J., *Journal. Mass Spectrometry*, 1997, 32, 677–688.

Griffey, R. H., et al., In *Proceedings of the 45th ASMS Conference on Mass Spectrometry and Allied Topics*, Palm Springs, CA, Jun. 1–5, 1997; p. 400.

Hage, D.S., et al., *Journal of Chromatography B*, 1997, 699, 499–525.

Hille, J., *Journal of Chromatography*, 1990, 502, 265–274.

Hoja, H., et al., *J Chromatogr B Biomed Sci Appl.*, 1997, 692, 329–335.

Hsieh, Y. F., et al., *J. Mol. Div.* 1996, 2, 189–196.

Hua, Y., et al., *Anal. Chem.*, 1995, 67, 1815–1823.

James, S., et al., *Anal. Biochem*, 1994, 217, 84–90.

Jemal, M., et al., *J Chromatogr B Biomed Sci Appl.*, 1997, 693, 109–116.

Kasai, Ken–Ichi, et al., *J. Chromatogr B Biomed Appl.*, 1986, 376, 33–47.

Klein, A., et al., *Glycobiology*, 1997, 7, 421–432.

Lam, K. S., *Anti–Cancer Drug Des.* 1997, 12, 145–167.

Lin, S., et al., *Anal. Chem.*, 1996, 68, 4087–4093.

Nedved, M. L., et al., *Anal. Chem.*, 1996, 68, 4228–4236.

Nelson, R. W., et al., *Anal. Chem.*, 1995, 67, 1153–1158.

Pais, P., et al., *J. Chromatogr A*, 1997, 775, 125–136.

Hasnoui, et al., "Screening of a large number of dyes for the separation of human immunoglobulin G2 from the other immunoglobulin G subclasses. Immunoglobulin G2 enrichment on immobilized Procion Yellow HE–4R", *J. Chromatogr.*, 766: 49–60 (1997).

Piperopoulos, G., et al., *J Chromatogr B Biomed Sci Appl.*, 1997, 695, 309–316.

Rouhi, A. M., *C&EN News*, p. 46–53 (Mar. 16, 1998).

Schriemer, D.C., et al., *Anal. Chem.*, 1996, 68, 3382–3387.

Stinson, S.C., *C&EN News*, p. 42–45, (Mar. 16, 1998).

Sweetnam, P. M., et al., In *Burger's Medicinal Chemistry and Drug Discovery*; M.E. Wolfe, Ed.; John Wiley & Sons: New York, 1995; pp. 697–731.

van Breeman, R. B., et al., *Anal. Chem.*, 1997, 69, 2159–2164.

Volmer, D.A., et al., *Anal. Chem.*, 1997, 69, 143–155.

Volmer, D.A., *Rapid Commun Mass Spectrom*, 1996, 10, 1615–1620.

Wieboldt, R., et al., *Anal. Chem.*, 1997, 69, 1683–1691.

Xue, Qifeng, et al., *Anal. Chem.*, 1997, 69, 426–430.

Zell, M., et al., *Rapid Commun Mass Spectrom*, 1997, 11, 1107–1114.

Zhao, Y. -Z., et al., *J. Med. Chem.*, 1997, 40, 4006–4012.

van Breemen, Richard B., et al., Pulsed Ultrafiltration Mass Spectrometry: A New Method for Screening Combinatorial Libraries., Analytical Chemistry (Jun. 1997), vol. 69, pp. 2159–2164.

Kasai, Ken–Ichi, et al., Frontal Affinity Chromatography: Theory for its Application to Studies on Specific Interactions of Biomolecules, Journal of Chromatography, (1986) vol. 376, pp. 33–47.

Blanar, et al. Interaction Cloning: Identification of a Helix–Loop–Helix Zipper Protein That Interacts with c–Fos. Science, vol. 26. May 15, 1992: 1014–1018.

Ellison, et al. Epitope–tagged Ubiquitin: A New Probe for Analyzing Ubiquitin Function. American Society for Biochemistry and Molecular Biology, 266:31, Nov. 5, 1991: 21150–21157.

Field, et al. Purification of a RAS–Responsive Adenylyl Cyclase Complex from *Saccharomyces cerevisiae* by Use of an Epitope Addition Method. Molecular and Cellular Biology, May 1988, 2159–2165.

Gerard, et al. Contruction and Expression of a Novel Recombinant Anaphylatoxin, C5a–N19, as a Probe for the Human C5a Receptor. Biochemistry 1990, 29, 9274–9281.

Hanke, et al. Construction of solid matrix–anibody–antigen complexes containing simian immunodeficiency virus p27 using tag–specific monoclonal antibody and tag–linked antigen. Journal of General Virology, 1992, 72, 653–660.

Herman, et al. Affinity Chromatography of DNA Labeled with Chemically Cleavable Biotinylated Nucleotide Analogs. Analytical Biochemistry, vol. 156, 1986, 48–55.

Hopp, et al. A Short Polypeptide Marker Sequence Useful for Recombinant Protein Identification and Purification. Bio/Technology, vol. 6, Oct. 1988, 1204–1210.

Kim, et al. Isolation of a Terminal Cisterna protein Which May Link theDihydropyridine Receptor to the Junctional Foot Protein in Skeletal Muscle. Biochemistry, 1990, 29, 9281–9289.

Kilmartin, et al. Rat Monoclonal Antitubulin Antibodies Derived by Using a New Nonsecreting Rat Cell Line. The Journal of Cell Biology, vol. 93, Jun. 1982, 576–582.

Lim, et al. Distribution and Specific Identification of Papillomavirus Major Capsid Preotein Epitopes by Immunocytochemistry and Epitope Scanning of Synthetic Peptides. Journal of Infectious Diseases 1990, 162, 1263–1269.

Lin, et al. Two–Step Affinity Chomatography, Model Systems and an Example Using Biotin–Avidin Binding and a Fluoridolyzable Linker. J. Org. Chem. 1991, 56: 6850–6856.

Pati. Novel vector for expression of cDNA encoding epitope–tagged proteins in mammalian cells. Gene, 1992, 114, 285–288.

Sassenfeld. Engineering proteins for purification. Tibtech, 1990, 8, 88–93.

Skinner, et al. Use of the Glu–Glu–Phe C–terminal Epitope for Rapid Purification of the Catalytic Doman of Normal and Mutant re GTPase–activating Proteins. The Journal of Biological Chemistry. 266:22, Aug. 5, 1991, 14163–14166.

Stammers, et al. Rapid purification and characterisation of HIV–1 reverse transcriptase and RnaseH engineered to incorporate a C–terminal tripeptide α–tubulin epitope. Febs Letters, 283:Jun. 2, 1991, 298–302.

von Zastrow, et al. Ligand–regulated Internalization and Recycling of Human β2–Adrenergic Receptors between the Plasma Membrane and Endosomes Containing Transferrin Receptors The Journal of Biological Chemistry, 67:Feb. 5, 1992, 3530–3538.

Wadzinski, et al. $NH_2$–terminal Modification of the Phosphatase 2A Catalytic Subunit Allows Functional Expression in Mammalian Cells. The Journal of Biological Chemistry, 267:Aug. 24, 1992, 16883–16888.

Translation of JPG –201650 A Jul. 1994, pp. 1–42.

English Abstract of JP –201650 A Jul. 1994, 1 page.

English Abstract of JP –6500396 Jun. 1994, 1 page.

English Abstract of JP 9–101306 Sep. 1997, 1 page.

English Abstract of JP 10–500951 Oct. 1998, 1 page.

Hutchens, et al., "Protein Interaction with Immobilized Ligangs: Quantitive Aalyses of Equilibrium Partition Data and Comparison with Analytical Chromatographic Approaches Using Immobilized Metal Affinity Adsorbants", *Anal. Biochem.*, 170: 168–182 (1988).

Kasai, et al., "Quantitative Analysis of Affinity Chromatography of Trypsin, A New Technique for Investigation of Protein–ligand Interaction", *J. Biochem.*, 77(1):261–264 (1975).

Katoh, et al., "Performance of Affinity Chromatography Columns", *Biotechnol. Bioeng.*, 20(2):267–280 (1978).

Ohyama, et al., "Frontal Affinity Chromatography of ovalbumin Glycoasparagines on a Concanavalin A–Sephrose Column", *J. Biol. Chem.*, 260(11): 6882–6887 (1985).

Wiebolt, et al., "Immunoaffinity Ultrafiltration with Ion Spray HPLC/MS, for Screeing Small–Molecule Libraries", *Anal. Chem.*, 69: 1683–1691 (1997).

Hage, et al., "Recent Advances in Chromatographic and Electrophoretic Methods for the Study of Drug–Protein Interactions", *J. Chromatograph. B*, 699: 499–525 (1997).

Kasai, et al., "Frontal Affinity Chromatography: Theory for its Application to Studies on Specific Interactions of Biomolecules", *J. Chromatogr.*, 376: 33–47 (1986).

Nelson, et al., "Mass Spectrometry Immunoassay", *Anal. Chem.*, 67: 1153–1158 (1995).

van Breeman, et al., "Pulsed Ultrafiltration Mass Spectrometry: A New Method for Screening Combinatorial Libraries", *Anal. Chem.*, 69:2159–2164 (1997).

J. Chromatogr., 379 (1986) (copy of content page of journal provided). (1 page).

Brekkan, et al., "Immobilized Membrane Vesicle or Proteoliposome Affinity Chromatography Frontal Analysis of Interactions of Cytochalasin B and D–Glucose with the Human Red Cell Glucose Transporter", *Biochemistry*, 35(37): 12141 –12145 (1996).

Zhang, et al.,, "Immoblized Nicotinic Receptor Stationary Phase for On–Line Liquid Chromatographic Determination of Drug–Receptor Affinities"*Anal. Biochem.*, 264:22–25 (1998).

* cited by examiner

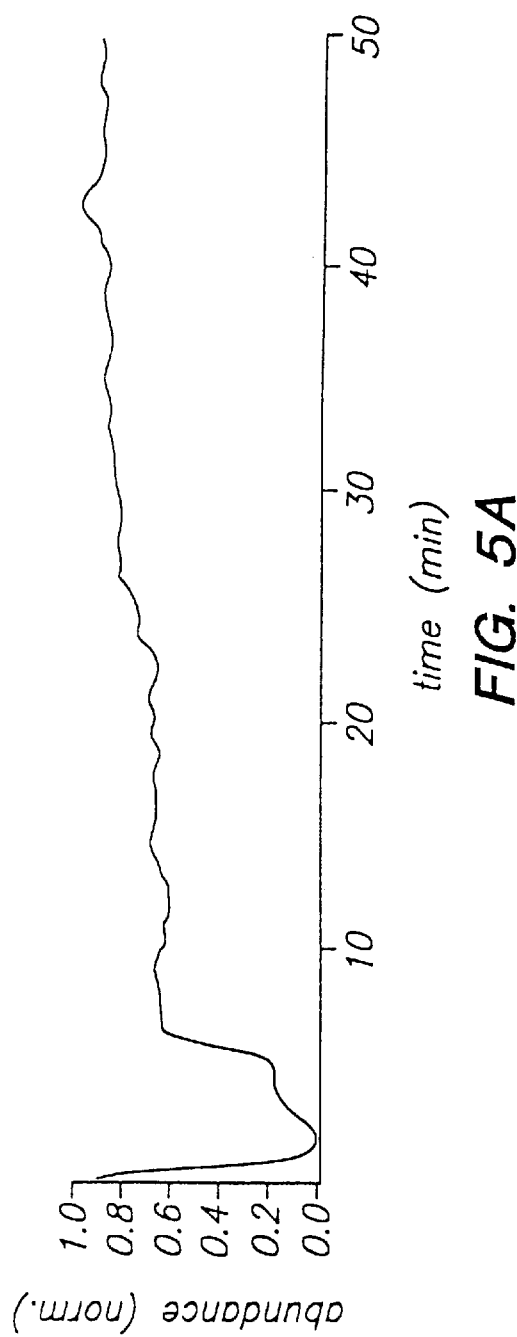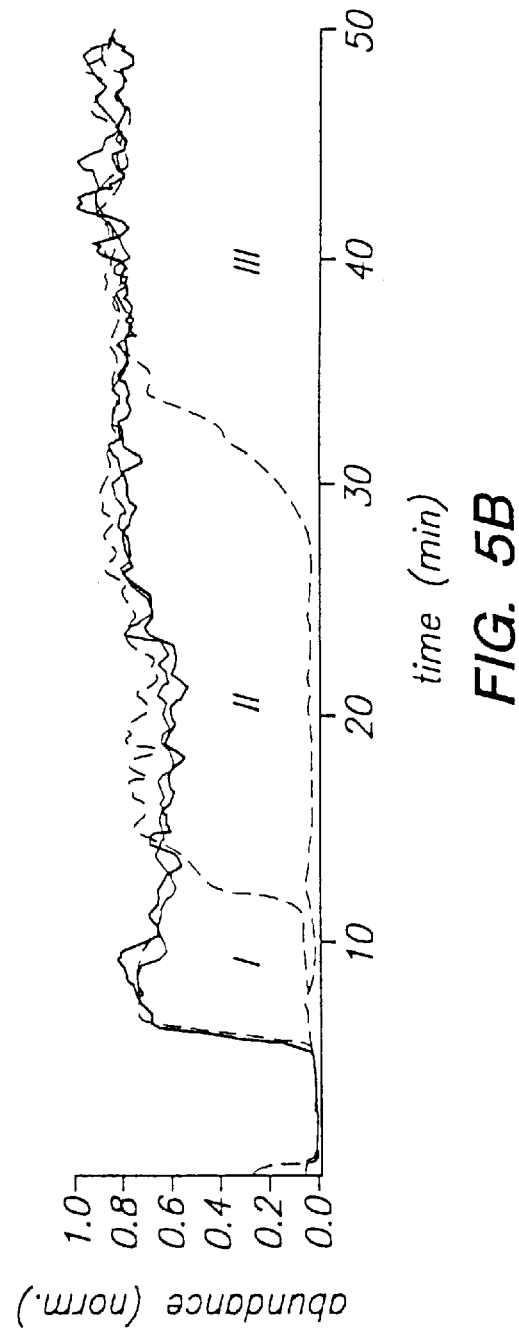

APPARATUS FOR SCREENING COMPOUND LIBRARIES

This application is a divisional, of application Ser. No. 09/069,890, filed Apr. 29, 1998, now U.S. Pat. No. 6,054,047.

CROSS-REFERENCE TO RELATED APPLICATIONS

This application claims the benefit of U.S. Provisional Application No. 60/079,622 filed Mar. 27, 1998, and entitled "Micro-Scale Frontal Affinity Chromatography Methods for the Screening of Compound Libraries," which application is incorporated herein by reference in its entirety.

BACKGROUND OF THE INVENTION

Field Of The Invention

This invention relates to apparatus for screening compound libraries, such as compound libraries generated using combinatorial chemistry techniques. The apparatus of this invention employ frontal chromatography in combination with mass spectrometry to screen a library of compounds to identify and rank those members of the library that bind to a target receptor. The apparatus of this invention also permit a compound library to be rapidly screened to determine if any member of the library has a higher affinity for the target receptor relative to a pre-selected indicator compound.

References

The following publications, patents and patent applications are cited in this application as superscript numbers:

[1] K. S. Lam, *Anti-Cancer Drug Des.* 1997, 12, 145–167.

[2] P. M. Sweetnam et al., In *Burger's Medicinal Chemistry and Drug Discovery;* M. E. Wolff, Ed.; John Wiley & Sons: New York, 1995; pp 697–731.

[3] R. H. Griffey et al., In *Proceedings of the 45th ASMS Conference on Mass Spectrometry and Allied Topics,* Palm Springs, Calif., Jun. 1–5, 1997; p. 400.

[4] L. Fang et al., In *Proceedings of the 45th ASMS Conference on Mass Spectrometry and Allied Topics,* Palm Springs, Calif., Jun. 1–5, 1997; p. 401.

[5] Y.-H. Chu et al., *J. Am. Chem. Soc.* 1996, 118, 7827–7835.

[6] Y.-Z. Zhao et al., *J. Med. Chem.* 1997, 40, 4006–4012.

[7] Y. F. Hsieh et al., *J. Mol. Div.* 1996, 2, 189–196.

[8] R. W. Nelson et al., *Anal. Chem.* 1995, 67, 1153–1158.

[9] D. C. Schriemer and L. Li, *Anal. Chem.* 1996, 68, 3382–3387.

[10] PCT/US97/07964 (International Publication No. WO 97/43641), published Nov. 20, 1997, entitled "Molecular Diversity Screening Device and Method."

[11] R. Wieboldt et al., *Anal. Chem.* 1997, 69, 1683–1691.

[12] R. B. van Breemen et al., *Anal. Chem.* 1997, 69, 2159–2164.

[13] M. L. Nedved et al., *Anal. Chem.* 1996, 68, 4228–4236.

[14] PCT/US95/03355 (International Publication No. WO 95/25737), published Sep. 28, 1995, entitled "Method for Identifying Members of Combinatorial Libraries."

[15] PCT/EP97/02215 (International Publication No. WO 97/43301), published Nov. 20, 1997, entitled "Identification of Members of Combinatorial Libraries By Mass Spectrometry."

All of the above publications, patents and patent applications are herein incorporated by reference in their entirety to the same extent as if each individual publication, patent or patent application was specifically and individually indicated to be incorporated by reference in its entirety.

State of the Art

In recent years, a large number of combinatorial chemistry techniques have been developed which permit vast libraries of diverse chemical compounds to be rapidly synthesized.[1] In combinatorial chemistry, a series of chemical reactions is typically conducted employing a plurality of reagents at each step to generate a library of compounds. Such techniques have the potential to greatly accelerate the discovery of new compounds having biologically useful properties by providing large collections of diverse chemical compounds for biological screening.

This ability to rapidly generate large collections of compounds using combinatorial chemistry techniques has created a need for new methods of screening compound libraries. The traditional approach of screening each compound individually in an assay to identify those compounds having the desired biological activity is no longer practical due to time and resource constraints. Thus, a need exists for new methods and apparatus which permit the rapid screening compound libraries.

In this regard, various methods for screening compound libraries have been reported. Typically, these screening methods involve the use of target receptors which have been labeled with fluorescent or other reporter groups.[2] In these methods, the compound library, typically bound to a resin bead, is exposed to the labeled target receptor and those members binding to the labeled target receptor are identified and physically separated. The particular ligand binding to the target receptor is then identified. In many of these techniques, elaborate procedures are required to keep track of individual members of the library. For example, coded tags are often added during the synthesis of the combinatorial library to allow the structure of the individual members to be subsequently determined. Alternatively, combinatorial libraries can be prepared in an array and the individual members of the library subsequently identified by their location in the array. While such methods can be effective, the need to keep track of individual members of the library during their synthesis and screening is quite cumbersome and often limits the type of synthetic procedures that can be employed. Additionally, many of these techniques require that the synthetic procedures be conducted on a solid phase, thus further limiting the synthetic procedures and reagents that can be used.

As an alternative, mass spectrometry is emerging as an important tool for the interrogation of combinatorial libraries. To date, mass spectrometry has been used to assess library quality[3,4] and, when coupled with molecular recognition technologies, has allowed for some success in the isolation and characterization of active library compounds.[5-15] Typically, when screening compound libraries for biologically active members, mass spectrometry is used in combination with a "capture and release" methodology. In this methodology, compound mixtures are presented to the target receptor, which is often immobilized on a solid support, and the resulting ligand-receptor complexes are separated from the unbound members of the library. After separation, the ligand-receptor complexes are typically denatured, for example, with a solvent and the solvent mixture containing the previously bound ligands is presented to the mass spectrometer to permit identification of the high affinity ligands.

For example, ultrafiltration has been used in combination with electrospray mass spectrometry to screen combinatorial libraries.[10-12] In this method, ligands present in a compound library are allowed to bind to a receptor and the resulting ligand-receptor complexes are purified by ultrafiltration. The ligand-receptor complexes are then dissociated using a solvent, such as methanol, and the previously bound ligands are detected by an electrospray mass spectrometer.

Affinity capillary electrophoresis (ACE) has also been coupled with mass spectrometry to screen combinatorial libraries.[5] In this procedure, ACE is used to separate ligand-receptor complexes from unbound ligands and mass spectrometry is used to identify the high affinity ligands.

Similarly, compound libraries have been screened using affinity chromatography in combination with mass spectrometry. For example, WO 97/43301 describes a method for characterizing the members of a combinatorial library, which method utilizes affinity selection in combination with mass spectrometry. Specifically, the members of the library are brought into contact with a domain of interest to allow for binding, i.e., the formation of a complex. After binding, the complex is separated from the unbound members of the library, typically by washing the unbound members from the column containing the complexes. The complexes are then treated to elute the bound library components and the eluted components are analyzed by mass spectrometry. The elution methods described include the use of displacers, chaotrope agents, pH elution, salt gradients, temperature gradients, organic solvents, selective denaturants and detergents. Using such methods, the weakly bound members of the library are purportedly eluted first and analyzed by mass spectrometry, followed by the elution of the more strongly bound members.

There are several disadvantages associated with the "capture and release" methods for screening compound libraries that have been previously reported. First, the procedure used to "release" the bound ligands from the ligand-receptor complexes may alter the binding profile for the various bound ligands, resulting in a false indication of binding strength. For example, using a pH gradient to release the bound members of the library may change the electronic character of the binding site on the receptor causing ligands which are strongly bound under physiological conditions to be prematurely released. Thus, the characterization of binding strength for various ligands based on their relative time of release may be misleading if the release conditions are different from the binding conditions. Accordingly, these methods may not accurately identify the most active members of a compound library. Additionally, certain conditions used for compound release, such as pH gradients, may irreversibly denature the receptor thus preventing its subsequent use for screening compound libraries.

Additionally, when "capture and release" methods are employed, each bound ligand is typically released over a relatively short period of time resulting, for example, in an elution peak or "spike" for each ligand. Accordingly, the effluent produced using such methods is typically monitored continually, for example, by mass spectrometry so that any particular elution peak is not missed. Thus, the number of analyzes that can be conducted using any particular mass spectrometer is limited. Accordingly, it would be desirable to develop methods and apparatus for screening compound libraries that do not rely upon "capture and release" methodologies.

SUMMARY OF THE INVENTION

This invention is directed to apparatus for screening compound libraries. The compound libraries may be generated or obtained by any means including, by way of example, combinatorial chemistry techniques or from fermentation broths, plant extracts, cellular extracts and the like. The apparatus of this invention employ frontal chromatography (FC) in combination with mass spectrometry (MS) to screen the library of compounds to identify and rank those members of the library that bind to a target receptor.

In frontal chromatography, a target receptor is typically immobilized on a suitable solid support material and packed in a column. A mixture containing putative ligands is then continuously infused through the column. Ligands having an affinity for the target receptor bind to the column, but eventually the capacity of the column for each ligand is exceeded and the ligands elute or "break through" at their infusion concentration. Once a ligand begins eluting from the column, it is continually present in the effluent. Compounds having little or no affinity for the target receptor break through earlier in the effluent compared to ligands having a higher affinity for the receptor.

In the present invention, mass spectrometry (MS) is employed to continuously or intermittently monitor the FC effluent. Using MS, the identity and break through time for each ligand on the column can be determined. Thus, FC-MS allows the relative affinity of each member of the library for the target receptor to be determined relative to other members of the library under ligand-receptor binding conditions. Using the present apparatus, an accurate ranking of the relative affinity of each member of the compound library for the target receptor can be ascertained.

Accordingly, in one of its apparatus aspects, the present invention is directed to an apparatus for screening a compound library to determine the relative or absolute affinity of a plurality of putative ligands to a target receptor, which apparatus comprises:

(a) a column comprising a target receptor optionally attached to a solid phase support and having a inflow end and an outflow end, wherein said column is capable of having a compound library comprising a plurality of putative ligands continuously applied thereto under frontal chromatography conditions whereby the target receptor is continuously contacted with the compound library to produce an effluent from the outflow end of the column;

(b) a first reservoir connected to the inflow end of said column for continuously applying the compound library to the column;

(c) a mass spectrometer connected to the outflow end of said column for continuously or intermittently analyzing the effluent from the column.

In a preferred embodiment, the above described apparatus further comprises:

(d) a second reservoir connected to the inflow end of the column for applying either (i) a mixture comprising the compound library and one or more indicator compounds, (ii) one or more indicator compounds, or (iii) a buffer solution to the column.

In another preferred embodiment, the above described apparatus further comprises:

(e) a third reservoir connected to the outflow end of the column for supplying a supplemental diluent to the effluent before analysis by the mass spectrometer.

Preferably, the column employed in this invention will have an internal diameter (i.d.) ranging from about 10 $\mu$m to about 4.6 mm. More preferably, the internal diameter of the column will be in the range of from about 100 $\mu$m to about 250 $\mu$m.

Preferably, the column will range in length from about 1 cm to about 30 cm, more preferably from about 2 cm to about 20 cm.

Preferably, the target receptor is selected from the group consisting of proteins, glycoproteins, glycosaminoglycans, proteoglycans, integrins, enzymes, lectins, selectins, cell-adhesion molecules, toxins, bacterial pili, transport proteins, receptors involved in signal transduction or hormone-binding, hormones, antibodies, major histocompatability complexes, immunoglobulin superfamilies, cadherins, DNA or DNA fragments, RNA and RNA fragments, whole cells, tissues, bacteria, fungi, viruses, parasites, preons, and synthetic analogs or derivatives thereof.

Additionally, the target receptor is preferably bound to a solid phase support. More preferably, the target receptor is covalently bound to the solid phase support or bound via biotin-avidin or biotin-streptavidin binding.

Preferably, the solid phase support used in this invention is selected from the group consisting of resin beads, glass beads, silica chips, silica capillaries and agarose.

The column employed in this invention preferably contains from about 1 pmol to about 10 nmol of target receptor active sites.

Preferably, the mass spectrometer employed in this invention is an electrospray mass spectrometer.

Additionally, since ligands continuously elute under FC conditions once they break though the column, FC-MS does not require constant effluent monitoring. Therefore, a plurality of FC-MS analyzes can be conducted simultaneously using a single mass spectrometer to intermittently monitor each column.

Accordingly, in another of its apparatus aspects, this invention provides an apparatus for screening a plurality of compound libraries to determine the relative or absolute affinity of a plurality of putative ligands in each library to a target receptor, which apparatus comprises:

(a) a plurality of columns each comprising a target receptor optionally attached to a solid phase support and each having a inflow end and an outflow end, wherein each of said columns is capable of independently having a compound library comprising a plurality of putative ligands continuously applied thereto under frontal chromatography conditions whereby the target receptor is continuously contacted with the compound library to produce an effluent from the outflow end of the column;

(b) a plurality of first reservoirs each connected to the inflow end of one of the columns for continuously applying a compound library to the columns;

(c) a mass spectrometer connected to the outflow end of each of said columns for intermittently analyzing the effluent from each of the column.

In a preferred embodiment, the above described apparatus further comprises:

(d) a plurality of second reservoirs each connected to the inflow end of one of the columns for applying either (i) a mixture comprising the compound library and one or more indicator compounds, (ii) one or more indicator compounds, or (iii) a buffer solution to the column.

In another preferred embodiment, the above described apparatus further comprises:

(e) a third reservoir connected to the outflow end of each of the columns for supplying a supplemental diluent to the effluent from each column before analysis by the mass spectrometer.

Preferably, the above described apparatus comprises from 2 to about 100 columns, more preferably from 3 to about 50 columns; and still more preferably from 5 to about 10 columns.

Preferably, each column is intermittently monitored for a period of about 0.5 seconds to about 10 seconds, preferably for about 1 second to about 5 seconds, before switching to the next column.

BRIEF DESCRIPTION OF THE DRAWINGS

FIG. 5A shows a total ion chromatogram (TIC) from a FC-MS run using six representative oligosaccharides having varying affinity for a carbohydrate-binding antibody that recognizes the 3,6-dideoxy-D-galactose (abequose) epitope in Salmonella paratyphi B O-antigens.

FIG. 5B shows selected ion chromatograms for the six oligosaccharides reconstructed from the TIC shown in FIG. 5A.

DETAILED DESCRIPTION OF THE INVENTION

Figure 1:
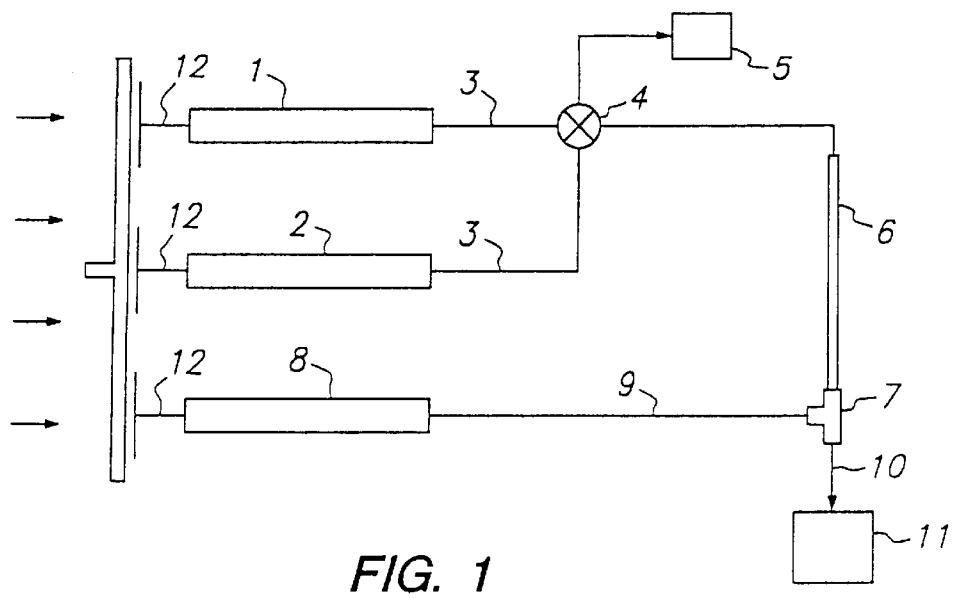
FIG. 1 illustrates a representative apparatus for screening compound libraries using frontal chromatography in combination with a mass spectrometer.

The present invention provides apparatus for screening compound libraries using frontal chromatography in combination with mass spectrometry. When describing the apparatus of this invention, the following terms have the following meanings, unless otherwise indicated. All terms not defined herein have their conventional art-recognized meaning.

Definitions

The term "break through time" refers to the period of time between elution of the void volume and the front corresponding to the elution of a particular compound during frontal chromatography.

The term "compound library" refers to a mixture or collection of one or more putative ligands generated or obtained in any manner. Preferably, the library contains more than one putative ligand or member.

The term "electrospray" refers to the generation of gas-phase ions from a flowing solution. Electrospray is typically performed at atmospheric pressure in an electric field with or without assisted nebulization and solvent evaporation.

The term "effluent" refers to the solvent or solution emerging or exiting from the frontal chromatography column.

The term "frontal chromatography conditions" refers to chromatography conditions in which a solution of putative ligands is applied or infused continuously at constant concentration through a column containing a target receptor such that the target receptor is continuously contacted with the putative ligands during the chromatography.

The term "indicator compound" refers to a compound having a known affinity or specificity for the target receptor and a measurable break through time under frontal chromatography conditions.

The term "ligand" refers to a molecule or group of molecules that bind to one or more specific sites of a receptor. Representative ligands include, by way of illustration, carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, lipids, retinoids, steroids, glycopeptides, glycoproteins, proteoglycans and the like, and synthetic analogues or derivatives thereof, including peptidomimetics, small molecule organic compounds and the like, and mixtures thereof. The term "putative ligand" refers to a ligand whose affinity or specificity for a target receptor, if any, has not been determined.

The term "microcolumn" refers to a column having an internal diameter less than or equal to about 1 mm.

The term "selected ion chromatogram" refers to a plot of ion abundance vs. time constructed from the intensity of a single ion. A selected ion chromatogram can be prepared from a scan or selected ion monitoring mode.

The term "selected ion monitoring" refers to the detection of a few pre-selected ions using a mass spectrometer (e.g. quadrupoles).

The term "solid support" or "solid phase support" refers to an inert material or molecule to which a target receptor may be bound or coupled, either directly or through a linking arm.

The term "synthetic small molecule organic compounds" refers to organic compounds generally having a molecular weight less than about 1000, preferably less than about 500, which are prepared by synthetic organic techniques, such as by combinatorial chemistry techniques.

The term "supplemental diluent" or "make-up flow" refers to a solution or solvent which is combined with the effluent from a column before the effluent passes into an electrospray mass spectrometer.

The term "target receptor" or "receptor" refers to a molecule or a group of molecules capable of binding a ligand at a specific site. Representative examples of target receptors include, by way of example, proteins, glycoproteins, glycosaminoglycans, proteoglycans, integrins, enzymes, lectins, selecting, cell-adhesion molecules, toxins, bacterial pili, transport proteins, receptors involved in signal transduction or hormone-binding, hormones, antibodies, major histocompatability complexes (MHCs), immunoglobulin superfamilies, cadherins, DNA or DNA fragments, RNA and RNA fragments, whole cells, tissues, bacteria, fungi, viruses, parasites, preons and the like; or synthetic analogs or derivatives of any of the above.

The term "target receptor active site" refers to the binding site of interest on a particular target receptor.

The term "total ion chromatogram" refers to a plot of ion abundance vs. time constructed from a summation of all ion intensities in a scan. In a total ion chromatogram, the number of scans are linearly related to time.

The term "void volume" or "$V_0$" refers to the volume of solution which passes through a frontal chromatography column from the point of infusion to the point of detection. Putative ligands having no affinity for the target receptor typically elute from column at the void volume.

The compound libraries employed in this invention may be prepared or obtained by any means including, but not limited to, combinatorial chemistry techniques, fermentation methods, plant and cellular extraction procedures and the like. Methods for making combinatorial libraries are well-known in the art. See, for example, E. R. Felder, *Chimia* 1994, 48, 512–541; Gallop et al., *J. Med. Chem.* 1994, 37, 1233–1251; R. A. Houghten, *Trends Genet.* 1993, 9, 235–239; Houghten et al., *Nature* 1991, 354, 84–86; Lam et al., *Nature* 1991, 354, 82–84; Carell et al., *Chem. Biol.* 1995, 3, 171–183; Madden et al., *Perspectives in Drug Discovery and Design* 2, 269–282; Cwirla et al., *Biochemistry* 1990, 87, 6378–6382; Brenner et al., *Proc. Natl. Acad. Sci. USA* 1992, 89, 5381–5383; Gordon et al., *J. Med. Chem.* 1994, 37, 1385–1401; Lebl et al., *Biopolymers* 1995, 37 177–198; and references cited therein. Each of these references is incorporated herein by reference in its entirety.

Any type of molecule that is capable of binding to a target receptor may be present in the compound library. For example, compound libraries screened using this invention may contain naturally-occurring molecules, such as carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, lipids, retinoids, steroids, glycopeptides, glycoproteins, proteoglycans and the like; or analogs or derivatives of naturally-occurring molecules, such peptidomimetics and the like; and non-naturally occurring molecules, such as "small molecule" organic compounds generated, for example, using combinatorial chemistry techniques; and mixtures thereof. The term "small molecule organic compound" refers to organic compounds generally having a molecular weight less than about 1000, preferably less than about 500.

A particular advantage of FC-MS is that compound libraries containing racemic mixtures may be screened to determine, for example, if only one isomer (e.g. an enantiomer or diastereomer) is binding to the target receptor, or if the isomers have different affinities for the target receptor. In this regard, if the isomers have different affinities for the target receptor, a different break through time will be observed for each isomer.

The compound libraries employed in this invention will typically contain a plurality of members or putative ligands. When a indicator compound is employed, the compound library will preferably contain less than about 50,000 members, more preferably, the compound library will contain less than about 10,000 members. When an indicator compound is not employed, the compound library will preferably contain less than about 10,000 members; more preferably, from 1 to about 1,000 members; and still more preferably, from about 5 to about 100 members.

The present apparatus is useful for analyzing the affinity of members of a compound library for any target receptor or domain which binds or complexes with a ligand. For example, the target receptor may be selected from, but is not limited to, proteins, glycoproteins, glycosaminoglycans, proteoglycans, integrins, enzymes, lectins, selecting, cell-adhesion molecules, toxins, bacterial pili, transport proteins, receptors involved in signal transduction or hormone-binding, hormones, antibodies, major histocompatibility complexes (MHCs), immunoglobulin superfamilies, cadherins, DNA or DNA fragments, RNA and RNA fragments, whole cells, tissues, bacteria, fungi, viruses, parasites, preons and the like; or synthetic analogues or derivatives of any of the above.

When employing the apparatus of this invention, the target receptor is optionally bound or coupled to a solid support. Preferably, the target receptor is covalently bound or coupled to the solid support. However, in some cases, such as when whole cells or organisms are employed as the target receptor, the cells or organisms may be contained within the column by using, for example, a porous frit at the outflow end of the column. Supports for receptors are well-known in the art and many are commercially available. Any such conventional support may be used in this invention. Representative supports include, by way of illustration, resin beads, glass beads, silica chips and capillaries, agarose, and the like. When silica capillaries are used as the solid support, the target receptor is bound directly to the walls of the column. Preferred solid supports for use in this invention include porous resin beads. A particularly preferred solid support is porous polystyrene-divinylbenzene polymer beads, such as POROS beads (available from Perseptive Biosystems, Framingham, Mass.).

The target receptor can be bound or coupled to the support using any art-recognized procedure. For example, the target receptor can be bound using direct immobilization techniques (i.e., covalent binding via a sulfhydryl, amino or carboxyl group and the like), covalent binding through a linking or spacer arm, biotin-avidin binding, biotin-streptavidin binding, antibody binding, GST-glutathione binding, ion exchange absorption, hydrophobic interaction, expression of the target receptor as a recombinant protein fused to maltose binding protein, fusion of the target receptor with a peptide which binds selectively to an affinity column, and the like. Such methods are well-known in the art and kits for practicing many of these methods are commercially available. See, for example, Stammers et al., *FEBS Lett.* 1991, 283, 298–302; Herman et al., *Anal. Biochemistry* 1986, 156, 48; Smith et al., *FEBS Lett.* 1987, 215, 305; Kilmartin et al., *J. Cell. Biol.* 1982, 93, 576–582; Skinner et al., *J. Biol. Chem.* 1991, 266, 14163–14166; Hopp et al., *Bio/Technology* 1988, 6, 1204–1210; H. M. Sassenfeld, *TIBTECH* 1990, 8, 88–93; Hanke et al., *J. General Virology* 1992, 73, 654–660; Ellison et al., *J. Biol. Chem.* 1991, 267, 21150–21157; U. K. Pati, *Gene* 1992, 114, 285–288; Wadzinski et al., *J. Biol Chem.* 1992, 267, 16883–16888; Field et al., *Mol. Cell. Biol.* 1988, 8, 2159–2165; Gerard et al., *Biochemistry* 1990, 29, 9274–9281; Ausselbergs et al., *Fibrinolysis* 1993, 7, 1–13; Hopp et al., *Biotechnology* 1988, 6, 1205–1210; Blanar et al., *Science* 1992, 256, 1014–1018; Lin et al., *J. Org. Chem.* 1991, 56, 6850–6856; Zastrow et al., *J. Biol. Chem.* 1992, 267, 3530–3538; Goldstein et al., *EMBO Jml.* 1992, 11, 0000—0000; Lim et al., *J. Infectious Disease* 1990, 162, 1263–1269; Goldstein et al., *Virology* 1992, 190, 889–893; and the articles in *IBI FLAG Epitope* Vol. 1: No. 1, September 1992; and references cited therein. Each of these references is incorporated herein by reference in its entirety.

In a preferred embodiment of this invention, the target receptor is bound or coupled to the solid support using biotin-avidin, biotin-streptavidin or a related-type binding. In this procedure, the target receptor is typically biotinylated with a biotin reagent containing a spacer arm. The biotinylated target receptor is then contacted with an avidin-containing solid support. The resulting biotin-avidin complex binds the target receptor to the solid support.

Procedures for biotinylating biomolecules are well-known in the art and various biotin reagents are commercially available. See, for example, E. A. Bayer et al., *Meth. Enzymol.* 1990, 184, 51; U. Bickel et al., *Bioconj. Chem.* 1995, 6, 211; H. Hagiwara et al., *J. Chromatog.* 1992, 597, 331; "Avidin-Biotin Chemistry Handbook" (available from Pierce, Rockford, Ill., Catalog Item No. 15055) and references cited therein. A preferred biotin reagent is NHS-LC-biotin (available from Pierce). The extent of biotin incorporation using such reagents can be monitored by, for example, matrix-assisted laser desorption/ionization as described in D. C. Schriemer and L. Li, *Anal. Chem.* 1996, 68, 3382–3387, or by other art-recognized methods as described in the "Avidin-Biotin Chemistry Handbook" (Pierce). Preferably, an average of about 1 to about 50 biotins are incorporated per target receptor, more preferably about 1 to about 10 biotins per target receptor.

The biotinylated target receptor is typically coupled with an avidin- or streptavidin-containing solid support or related material. Such supports are commercially available or can be prepared by art-recognized procedures. Preferred avidin-containing supports include Ultralink-immobilized avidin (available from Pierce) and POROS 20 immobilized streptavidin (available from Perseptive Biosystems). The biotinylated target receptor is typically coupled with the avidin-containing support by contacting the receptor with the support in a suitable buffer, such as phosphate buffered saline (pH 7), for about 0.5 to 4 hours at a temperature ranging from about 4° C. to about 37° C. Preferably, after coupling the biotinylated target receptor to the avidin-containing support, any remaining avidin binding sites on the support are blocked by contacting the solid support with an excess of free biotin.

The target receptor may be bound or coupled to the solid support either prior to or after introducing the solid support material into a column. For example, the biotinylated target receptor may be contacted or incubated with the avidin- or streptavidin-containing solid support and the resulting solid support containing the target receptor subsequently introduced into a column. Alternatively, the avidin- or streptavidin-containing solid support can be first introduced into the column and the biotinylated target receptor then cycled through the column to form the solid support containing the target receptor in the column. Either of these methods may also be used with any of the other previously mentioned procedures for coupling the target receptor to the solid support.

The solid support material may be introduced into the column using any conventional procedure. Typically, the solid support is slurried in a suitable diluent and the resulting slurry is pressure packed or pumped into the column. Suitable diluents include, by way of example, buffers such as phosphate buffered saline (PBS) solutions, preferably containing a preservative such as sodium azide, and the like.

Generally, the activity of the target receptor will determine the size of the column employed in this invention, i.e., a smaller column volume may be employed when the target receptor has more activity per unit column volume. Typically, the column employed in this invention will have an internal diameter (i.d.) ranging from about 10 $\mu$m to about 4.6 mm. Preferably, the internal diameter of the column will be in the range of from about 100 μm to about 250 μm. The column will typically range in length from about 1 cm to about 30 cm, preferably from about 2 cm to about 20 cm. Preferably, the column will have from about 1 pmol to about 10 nmol of target receptor active sites per column; more preferably, from about 10 pmol to about 250 pmol of target receptor active sites per column.

If an indicator compound is employed, the length of the column and its i.d. will also depend upon the $K_d$ of the indicator compound (i.e., a smaller column may be used when the indicator has a higher affinity for the target receptor). Preferably, when an indicator is employed, the column length and i.d. are selected so that the indicator compound elutes a measurable quantity after the void volume.

The body of the column employed in this invention may be comprised of any conventional column body material including, by way of illustration, poly(ether ether ketone) (PEEK), fused silica, silicon microchips, stainless steel, nylon, polyethylene, polytetrafluoroethylene (Teflon) and the like. Preferably, the column body is comprised of poly(ether ether ketone).

After the solid support containing the target receptor is introduced or formed in the column, the column is typically flushed with a suitable diluent to remove any unbound target receptor or impurities. Suitable diluents for flushing the column include, for example, phosphate buffered saline, TRIS buffers and the like. If desired, a detergent may also be included in the buffer to facilitate removal of unbound target receptor or impurities.

After the column is flushed, the column is typically equilibrated with a buffer suitable for frontal chromatography and compatible with mass spectrometry. Volatile buffers are generally preferred for use with mass spectrometry. For frontal chromatography, a buffer is typically selected to promote receptor-ligand interaction. Suitable buffers for use in FC-MS include, by way of example, ammonium acetate, ammonium formate and the like.

Following equilibration of the column, the compound library is then continuously applied to the column under frontal chromatography conditions. Typically, when applied to the column, the compound library comprises a solution of the library members or putative ligands in a suitable diluent. Typically, the diluent is the buffer solution used to equilibrate the column. Generally, the concentration of the library members in the diluent will range from about 0.01 μM to about 50 μM. Preferably, the concentration of library members ranges from about 0.1 μM to about 10 μM.

Procedures for conducting frontal chromatography are well-known in the art. See, for example, K.-I. Kasai et al., *Journal of Chromatography* 1986, 376, 33–47; D. S. Hage et al., *Journal of Chromatography B*, 1997, 669, 449–525 and references cited therein. The disclosures of these references are incorporated herein by reference in their entirety. Typically, the compound library is continuously applied or infused into the column containing the target receptor. Under these conditions, the target receptor is continuously contacted or challenged with each of the members of the compound library. The column is driven to dynamic equilibrium by continuously applying the compound library to the column. Library members having different binding constants to the target receptor display different break through times or hold-up volumes on the column, i.e., those members having a higher affinity for the target receptor have a longer break through time on the column or a larger hold-up volume until they begin to elute from or break-though the column at their initial infusion concentration. Unlike zonal chromatographic methods, no physical separation of the library members is achieved using frontal chromatography. Suitable methods for conducting FC-MS are described in U.S. patent application Ser. No. 09/070,131, filed on even date herewith, and entitled "Methods for Screening Compound Libraries," the disclosure of which is incorporated herein by reference in its entirety During the frontal chromatography, the column is typically at a temperature in range from about 0° C. to about 90° C.; preferably from about 4° C. to about 60° C.; more preferably from about 20° C. to about 40° C.

When a ligand has a very high affinity for the target receptor, it may be desirable to pre-equilibrate the column with the compound library before conducting the FC-MS analysis. The column can be pre-equilibrated by either by infusing the compound library through the column for a period sufficient to allow the column to reach equilibrium, i.e., for about 0.25 to 24 hours, or by infusing the compound library into the column, stopping the flow, and allowing the system to come to equilibrium for a period of up to one day before conducting the analysis. If desired, a sequence of stop-flow cycles may also be conducted.

In the apparatus of this invention, a mass spectrometer is coupled to the column to analyze the effluent. Mass spectrometry is particularly useful in the present invention since it allows for both detection and identification of the library members present in the effluent. In this regard, mass spectrometry allows the eluting members of the library to be identified based on their mass/charge ratio.

Prior to analyzing the effluent from the column by mass spectrometry, the effluent is optionally diluted with a supplemental diluent or "make-up flow" and the combined flow is directed into, for example, the electrospray mass spectrometer. Typically, the supplemental diluent comprises a major amount of an organic solvent and a minor amount of an aqueous buffer. The organic solvent is selected so as to promote a stable and efficient electrospray. Representative organic solvents suitable for use in the supplemental diluent include, by way of example, acetonitrile, methanol, isopropanol and the like. A preferred organic solvent is acetonitrile. Typically, the amount of supplemental diluent employed is adjusted so that the combined flow rate of the effluent and the supplemental diluent is less than about 100 μL/min. Preferably, the combined flow rate entering the mass spectrometer ranges from about 100 nL/min to about 20 μL/min.

Methods for analyzing effluents using mass spectrometry are well-known in the art. Any type of mass spectrometry which is capable of directly or indirectly analyzing the components present in a solution may be employed in this invention including, for example, electrospray mass spectrometry (ES-MS), atmospheric pressure chemical ionization (APCI), membrane introduction mass spectrometry (MIMS), continuous flow fast atom bombardment (cf-FAB), thermospray techniques, particle beam, moving belt interfaces and the like. Electrospray mass spectrometry is particularly preferred. Apparatus and techniques for conducting electrospray mass spectrometric analysis are described, for example, in S. J. Gaskell, *"Electrospray: Principles and Practice"*, *J. Mass. Spectrom.* 1997, 32, 677–688 and reference cited therein. The mass spectrometer may be of any type (i.e., scanning or dynamic) including, by way of illustration, quadrupole, time of flight, ion trap, FTICR and the like.

Typically, the mass spectrometer parameters are set to provide the highest sensitivity for the eluting compounds.

Generally, when an electrospray mass spectrometer is employed, such adjustments will involve optimization of, for example, nebulizer pressure, drying gas flow rate, ion transmission and electrospray needle position. For example, the nebulizer pressure will typically range from about 0 psi to about 60 psi; and the drying gas flow rate will range from about 0 L/min to about 50 L/min. A total ion chromatogram is typically measured and monitored in real-time. The size of the column, the concentration of the compound library and the flow rate will generally determine the run-time. Typical run times range from about 1 min to about 60 min.

Upon completion of the frontal chromatography, the column is typically regenerated by washing with a large volume of the binding buffer, with or without a competitive ligand. In this regard, a particular advantage of the present method is that denaturing of the target receptor is not required at any point in the procedure. Accordingly, columns may be re-used many times generally with no observable loss of activity or leaching of the target receptor.

A representative apparatus for conducting the screening methods of this invention is illustrated in FIG. 1. As shown in FIG. 1, a first reservoir 1, containing a buffer solution, and a second reservoir 2, containing a solution of a compound library in a buffer, are connected via tubing 3 to valve 4. In FIG. 1, reservoirs 1 and 2 are syringes although any similar reservoir may be employed. Valve 4 allows the solutions from reservoirs 1 or 2 to be directed into a waste container 5 or into the inflow end of column 6. Column 6 contains the target receptor bound to a solid phase support, the column wall or otherwise retained within the column. The outflow end of column 6 is connected to a mixing tee 7, which is also connected to reservoir 8, containing a supplemental diluent, via tubing 9. The effluent from column 6 is mixed with the supplemental diluent from reservoir 8 in mixing tee 7 and the outflow is directed via tubing 10 to an electrospray mass spectrometer 11. To control the flow from reservoirs 1, 2 and 8, pressure is applied to plungers 12 via, for example, a pump.

In another of its embodiments, the apparatus of this invention can be used to screen a compound library to determine if any member of the library has an affinity for a target receptor that interferes with the binding of a pre-selected indicator compound or a mixture of indicator compounds. In this embodiment, the break through time of an indicator compound having a known affinity for the target receptor is determined after the column has been equilibrated with the compound library and compared to the break through time for the indicator compound in the absence of the compound library. If the indicator compound has a shorter break through time after equilibration with the compound library, the compound library contains one or more ligands having an overall affinity for the target receptor which is higher than the indicator compound. Since an indicator compound can be selected having a relatively short break through time on the column, a significant advantage of this embodiment is that compound libraries can be rapidly screened, e.g., in less than 5 minutes, to identify those libraries having a pre-determined minimum level of affinity for the target receptor. When a library is identified as having the pre-determined minimum level of affinity for the target receptor, the library can be further analyzed using FC-MS to identify the ligands binding to the target receptor.

One advantage of using a indicator compound is that the screening time for each library is significantly reduced since only the indicator compound needs to be monitored. Additionally, since the indicator compound binds to the target receptor at the active site of interest, a change in the break through time for the indicator is only observed when a member of the library binds to the same active site as the indicator compound. Accordingly, non-specific binding of the library to the target receptor does not provide false leads.

The indicator compound used in this embodiment of the invention is typically selected so as to have a relatively weak affinity for the target receptor. This permits the indicator compound to rapidly elute or break through the column, thus shortening the period of time necessary to monitor the effluent. An indicator compound having a break through time on the column less than about 5 minutes in the absence of the compound library is preferred. Alternatively, an indicator having a strong affinity for the target receptor may be used thereby allowing smaller columns to be employed. When an indicator compound having a strong affinity is used, the compound library will typically be applied to the column at a higher concentration. The break through time for the indicator compound on the column in the absence of the compound library is determined using the FC-MS procedures described herein. The affinity of the indicator compound for the target receptor can be determined using conventional techniques, such as microcalorimetry and the like; or by using the FC-MS methods of this invention. Preferably, the indicator compound will also have a unique mass in comparison to the members of the compound library so that the indicator compound can be unambiguously identified by mass spectrometry. Generally, when using an indicator compound and a quadrupole mass spectrometer, only the mass of the indicator compound is monitored to provide for better sensitivity.

Representative examples of indicator compounds suitable for use with specific target receptors include, by way of illustration, $\alpha Abe(1\rightarrow 3)\alpha Tal\text{-}OCH_3 (K_d=0.2 \text{ mM})$ for use with a monoclonal antibody that recognizes the 3,6-dideoxy-D-galactose (abequose) epitope in *Salmonella paratyphi* B O-antigens; phytic acid ($K_d=1$ $\mu M$) for use with L-selectin, and the like. Additionally, more than one indicator compound may be employed. The indicator may also be coupled or conjugated to another molecule or contain an atom or isotope which facilitates its detection. For example, the indicator compound can be conjugated to polyethylene glycols (PEGs) so that the mass spectra would contain peaks differing by 44 units thereby facilitating detection of the of indicator compound.

When using an indicator compound, the break through time for the indicator compound is first determined by applying the indicator compound to the column containing the target receptor under frontal chromatography conditions. The column is then typically equilibrated with the compound library to be screened. Generally, the compound library is applied or infused into the column for a time sufficient to allow all of the library members to break through the column. In some cases, such as when very strong binding ligands are present, not all members of the library will achieve equilibrium. The effluent during this period may be presented to the mass spectrometer for analysis or may be collected for recycling or disposal. Once the column has been equilibrated (or partially equilibrated) with the compound library, a mixture comprising the compound library and the indicator compound is applied to or infused into the column using the frontal chromatography procedures described herein. Preferably, the indicator compound will be present in the mixture in an amount ranging from about 1 nM to about 10 $\mu M$, more preferably from about 10 nM to about 100 nM. The effluent from the column is analyzed to determine the break through time for the indicator compound on the compound library-equilibrated column and this time period is compared to the pre-determined break through time for the indicator compound to ascertain whether the compound library has a higher affinity for the target receptor relative to the indicator compound.

Alternatively, the indicator compound alone can be applied or infused into the column after equilibration of the column with the compound library. This technique would allow very strongly bound ligands or those with slow off rates to be detected.

In addition to detecting the indicator compound using mass spectrometry, it is also contemplated that other methods of detection may be employed. For example, an indicator compound can be detected in the effluent from the column using, by way of example, fluorescence, infra-red absorption, UV-visible absorption, nuclear magnetic resonance (NMR), atomic spectroscopy (i.e., AAS, ICP-OES, etc.), flow cytometry and the like.

The apparatus of this invention allow a plurality of FC-MS analyses to be conducted simultaneously using a single mass spectrometer to intermittently monitor each column. Unlike "capture and release" methods which typically provide an elution peak or "spike" for each ligand, FC-MS does not require constant effluent monitoring because once a library member breaks through the column, that member is continuously present in the effluent and can be detected by the mass spectrometer. Therefore, a plurality of FC-MS analyses can be conducted simultaneously using a single mass spectrometer to intermittently monitor each column. For example, using this invention, at least about 100 columns can be conducted simultaneously.

When employing multiple columns, each column is typically monitored for a brief period of time before switching to the next column. For example, with a quadrupole mass spectrometer, each column is typically monitored sequentially for a period of about 0.5 seconds to about 10 seconds, preferably for about 1 second to about 5 seconds, before switching to the next column. The effluent from each column is analyzed as described herein using mass spectrometry. Generally, a single running file is used to collect all of the data from the multiple column thereby generating a composite total ion chromatogram. Subsequently, separate total ion chromatograms for each column are recreated by synchronizing column switching with mass spectrometry data acquisition.

In a preferred embodiment, each column will have an individual electrospray needle for injection of the column's effluent into the electrospray mass spectrometer. Any geometric arrangement of multiple electrospray needles that allows for fast and repetitive sequences of needle advancement may be employed. A suitable apparatus for the injection of multiple effluents into an electrospray mass spectrometer is described in U.S. patent application No. 09/069,656, filed on even date herewith, and entitled "Device for Delivery of Multiple Liquid Sample Streams to a Mass Spectrometer," the disclosure of which is incorporated herein in its entirety. Alternatively, a linear moving row of electrospray needles (sprayers) and the like may be employed. See, for example, Q. Xue et al., *Anal. Chem.* 1997, 69, 426–430 and references cited therein, the disclosed of which is incorporated herein by reference in its entirety.

Figure 2:
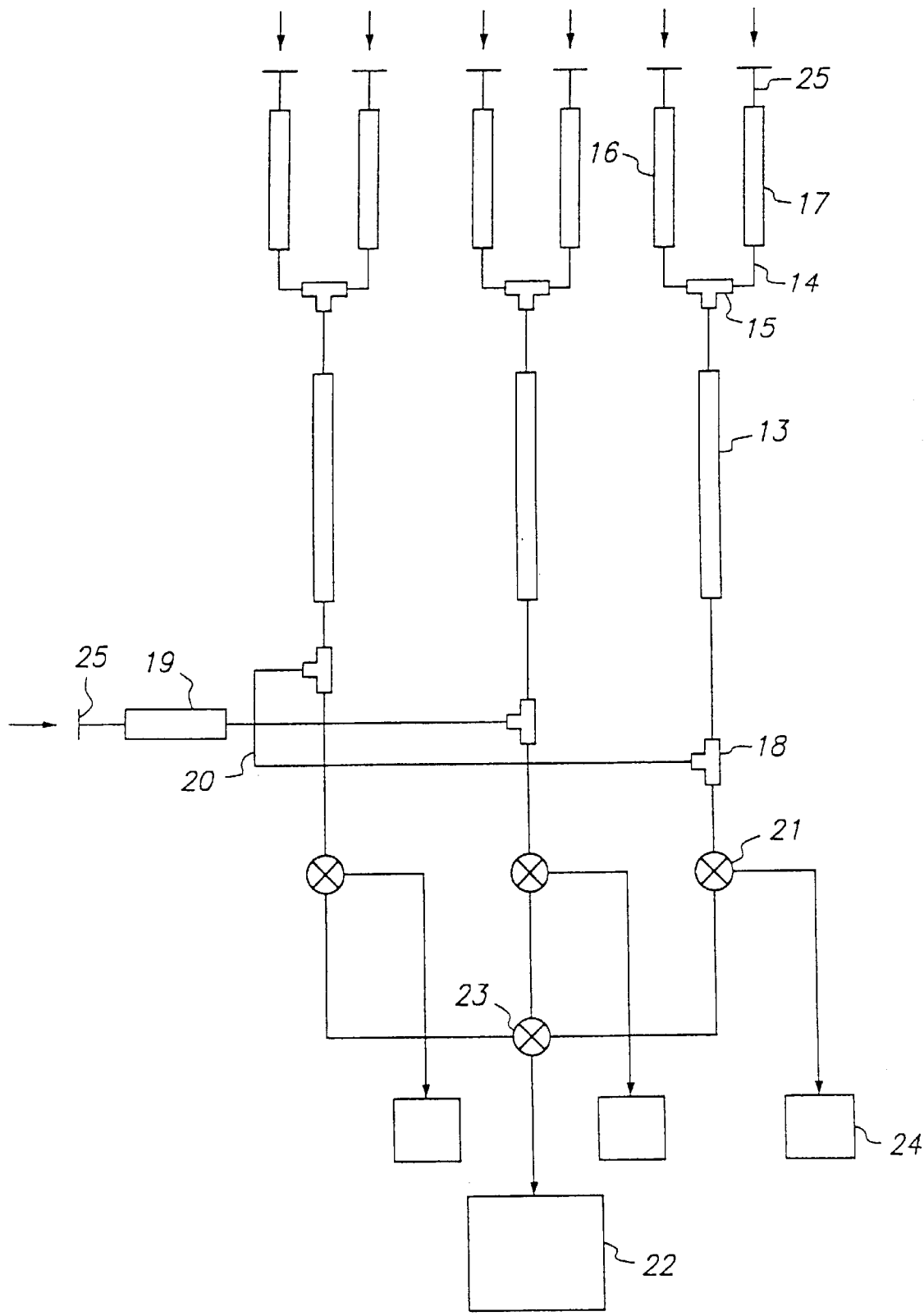
FIG. 2 illustrates a representative apparatus for screening compound libraries using a plurality of frontal chromatography columns in combination with a mass spectrometer.

A representative apparatus for screening compound libraries using a plurality of columns is illustrated in FIG. 2. As shown in FIG. 2, each of a plurality of columns 13 is connected via tubing 14 and mixing tee 15 to a first reservoir 16, containing a solution of a compound library in a binding buffer, and a second reservoir 17, containing the binding buffer. In FIG. 2, reservoirs 16 and 17 are syringes although any similar reservoir may be employed. Each column 13 contains a target receptor bound to a solid phase support. The buffer solution in reservoir 17 is used to wash column 13 before or after introduction of the compound library. The outflow end of each column 13 is connected to a mixing tee 18, which is also connected to reservoir 19, containing a supplemental diluent, via tubing 20. The effluent from each column 13 is mixed with the supplemental diluent from reservoir 19 in mixing tees 18 and the outflow is directed via tubing 20 and valves 21 into an electrospray mass spectrometer 22, via an electronically-actuated multi-port selection valve 23, or into waste/recovery containers 24. To control the flow from reservoirs 16, 17 and 19, pressure is applied to plungers 25 via, for example, pumps.

Figure 3:
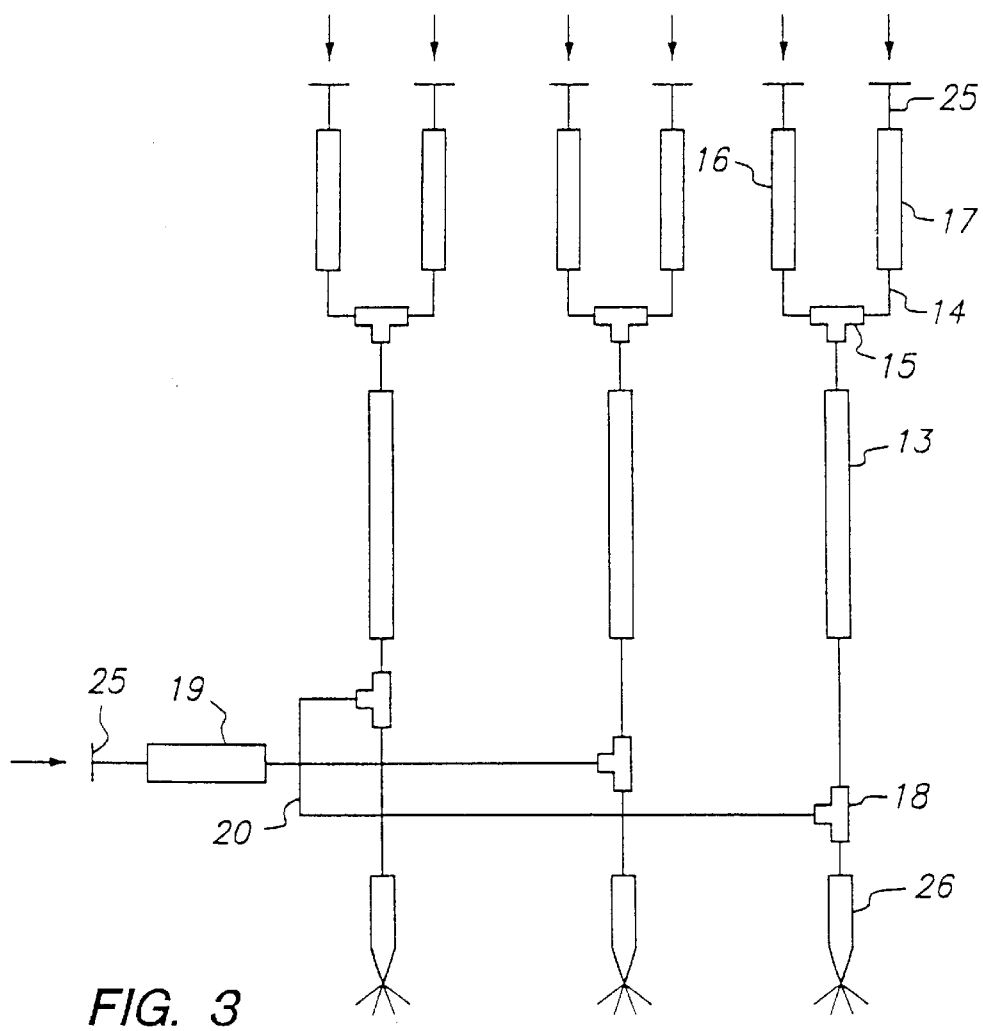
FIG. 3 illustrates another representative apparatus for screening compound libraries using a plurality of frontal chromatography columns in combination with a mass spectrometer.

Alternatively, in another embodiment illustrated in FIG. 3, the outflow from mixing tees 18 may be directed via tubing 20 into individual electrospray needles 26 for mass spectrometer analysis.

When using a plurality of columns to evaluate compound libraries using a indicator compound, each column may be run sequentially, if desired, since the run time for each of the columns is relatively short, i.e., typically about 3 minutes per column. When using an indicator compound, sequential runs of multiple columns may be advantageous since this allows the retention time for the indicator compound to be more accurately determined.

Figure 4:
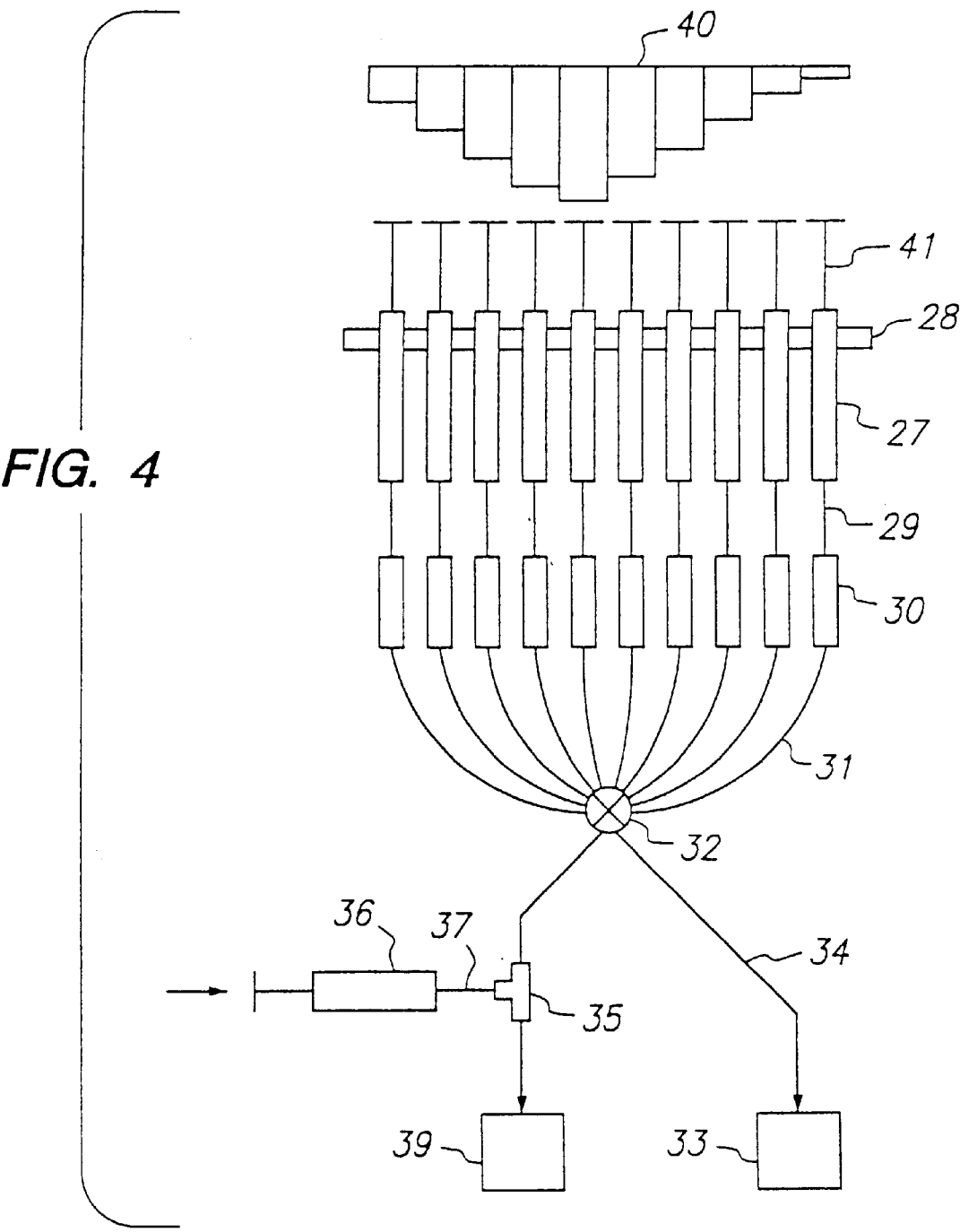
FIG. 4 illustrates a representative apparatus for sequentially screening compound libraries with an indicator compound using a plurality of frontal chromatography columns in combination with a mass spectrometer.

A representative apparatus for sequentially screening compound libraries with a indicator compound using a plurality of columns is illustrated in FIG. 4. As shown in FIG. 4, a plurality of reservoirs 27 (e.g., syringes) are held in place with clamp 38. Each reservoir 27 contains a mixture of a compound library and an indicator compound in a suitable diluent (or, alternatively, simply the indicator). The end of each reservoir 27 is connected via tubing 29 to the inflow end of a column 30 containing the target receptor bound to a solid phase support. The outflow end of each column 30 is connected via tubing 31 to an electronically-actuated multiport stream selection valve 32 which controls the flow of the effluent from columns 30. Using valve 32, the effluent from the columns may be directed into a waste container 33, via tubing 34, or into mixing tee 35, via tubing 36. Mixing tee 35 is also connected to reservoir 36, containing a supplemental diluent, via tubing 37. The effluent from each column 30 is mixed with the supplemental diluent from reservoir 36 in mixing tee 35 and the outflow is directed via tubing 38 into an electrospray mass spectrometer 39. To control the flow from the reservoirs 27 into columns 30, a stand-off block 40 may be employed. When pressure is applied to stand-off block 40 via, for example, a pump, the plunger 41 of each reservoir 27 is individually depressed in sequence thereby infusing the contents of the reservoir through tubing 29 into the corresponding column 30. The effluent emerging from each column 30 is sequentially directed into mass spectrometer 39 for analysis.

The apparatus of this invention also permit the absolute affinity or dissociation constant, $K_d$, for certain individual members of a compound library to be readily determined. In this regard, ligands having an affinity for the target receptor break through the column at volumes (i.e., break through times) related to their concentrations and $K_d$ values, according to the following equation:

$$V_x - V_0 = \frac{B_t}{[X]_0 + (K_d)_x}$$

where $B_t$ represents the dynamic binding capacity of the column; $[X]_0$ is the infusion concentration of the ligand in the compound library; $K_d$ is the dissociation constant for the ligand; $V_0$ is the void volume; and $V_x$ represents the volume at the mid-point of the front corresponding to the break through of the ligand. This simple equation indicates that, once $B_t$ and the concentration of the ligand are known, the dissociation constant of a ligand can be determined from a single measurement of its $V_x$-$V_0$.

In order to determine $B_t$, a representative compound, e.g., compound X, is infused through the column at various concentrations and the corresponding $V_x$-$V_0$ values measured. A plot of $([X]( V-V_0))^{-1}$ versus $[X]^{-1}$ is generated, where the y-intercept indicates the dynamic binding capacity of the column ($B_t$) (analogous to a Lineweaver-Burk plot).

Once the dynamic binding capacity of the column has been determined, the dissociation constants for individual members of the compound library can be determined from a single FC-MS run. For example, the $K_d$ for compounds where $[X]<<(K_d)_x$ is determined simply from $B_t/(V-V_0)$. For those members of the library with a low dissociation constant, knowledge of their concentration or infusion of the compound library at higher dilution is required to determine $K_d$.

The following examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| $B_t$ | =dynamic binding capacity |
| ° C. | =degrees Celsius |
| cm | =centimeter |
| eq. | =equivalents |
| FAB | =fast atom bombardment |
| FC | =frontal chromatography |
| g | =grams |
| $K_d$ | =dissociation constant |
| L | =liter |
| MALDI | =matrix-assisted laser desorption/ionization |
| meq. | =milliequivalent |
| mg | =milligram |
| mL | =milliliter |
| mM | =millimolar |
| mmol | =millimole |
| MS | =mass spectrometry |
| m/z | =mass charge ratio |
| N | =normal |
| PBS | =phosphate buffered saline |
| PEEK | =poly(ether ether ketone) |
| pmol | =picomole |
| TIC | =total ion chromatogram |
| $\mu$g | =micrograms |
| $\mu$L | =microliter |
| $\mu$m | =micrometer |
| $\mu$M | =micromolar |
| $V_0$ | =void volume |

Example 1

Screening of an Oligosaccharide Library Using FC-MS

In this example, a compound library containing a mixture of six oligosaccharides was screened using frontal chromatography in combination with an electrospray mass spectrometer to determine the relative affinity of the oligosaccharides for a monoclonal antibody that recognizes the 3,6-dideoxy-D-galactose (abequose) epitope in *Salmonella paratyphi* B O-antigens.

The compound library consisted of the following six oligosaccharides: $\alpha$GalNAc(1→3)$\beta$Gal-OGr (compound 1); $\alpha$Gal(1→3)[$\alpha$Fuc(1→2)]$\beta$Gal-OGr (compound 2); $\alpha$Man(1→3)[$\alpha$Man(1→6)]$\beta$Man-OGr (compound 3); $\alpha$Abe(1→3)$\alpha$Tal-OCH$_3$ (compound 4); $\alpha$Gal(1→2)[$\alpha$Abe(1→3)]$\alpha$Man-OCH$_3$ (compound 5); and $\alpha$Glc(1→4)$\beta$Glc(1→4)$\alpha$Gal(1→2)-[$\alpha$Abe(1→3)]$\alpha$Man(1→3)$\alpha$Glc(1→4)$\beta$Glc-OCH$_3$ (compound 6), wherein Gr=O(CH$_2$)$_8$CO$_2$CH$_3$. Compound 1–3 were obtained using the procedures described in U.S. Pat. No. 4,362,720 to R. U. Lemieux et al., issued Dec. 7, 1987; U.S. Pat. No. 4,137,401 to R. U. Lemieux et al, issued Jan. 30, 1979; and K. J. Kaur et al., "Use of N-Acetylglucosaminyltransferases I and II in the Preparative Synthesis of Oligosaccharides", *Carbohydr. Res.* 1991, 210, 145–153; respectively, the disclosures of which are incorporated herein by reference in their entirety. Compounds 4–6 were obtained using the procedures described in D. R. Bundle et al., "Modulation of Antibody Affinity by Synthetic Modifications of the Most Exposed Pyranose Residue of A Trisaccharide Epitope", *Bioorg. Med. Chem.* 1994, 2, 1221–1229, the disclosure of which is incorporated herein by reference in its entirety. Compounds 1–3 are known to have no specificity for the antibody. On the other hand, compounds 4–6 contain the minimal requirement for recognition (abequose) and span a range of affinity for the antibody. The $K_d$ values for compounds 4–6, as determined by titration microcalorimetry, are shown in Table 1 below.

The monoclonal antibody used in this experiment was produced as described in D. R. Bundle et al, "Molecular Recognition of a Salmonella Trisaccharide Epitope by Monoclonal Antibody Se155.4" *Biochem.* 1994, 33, 5172–5182. The antibody (0.5 mg) was biotinylated with a biotin reagent containing a long-chain spacer arm (NHS-LC-biotin, Pierce). The extent of biotin incorporation was monitored by matrix-assisted laser desorption/ionization and the reaction was terminated at 14 biotins/IgG (average). The biotinylated antibody was then coupled to a beaded support by incubating the antibody with 25 $\mu$L of Ultralink immobilized avidin (Pierce, Cat. No. 53119) in bicarbonate buffer (pH 8.5) for 1 hour. The beads were then thoroughly washed with the bicarbonate buffer. A UV quantitation indicated an immobilization of ~45 $\mu$g antibody/25 $\mu$L beads was achieved. The beads were then slurry-packed into a 500 $\mu$m i.d. by 11.5 cm poly(ether ether ketone) (PEEK) column body (~23 $\mu$L column volume).

In this experiment, a mixing tee served a dual role as a column end-fitting and mixing chamber for the column eluent and organic make-up flow. The column was then directly connected to an electrospray mass spectrometer (Hewlett-Packard series 1100 MSD, single quadrupole).

For operation in frontal chromatography mode, the column was first flushed with ammonium acetate buffer (NH$_4$OAc, 2 mM, pH 6.7). After flushing, the flow was switched to a second solution containing a mixture of the six oligosaccharides in ammonium acetate buffer, each present at 1 $\mu$M. All solutions were infused concurrently with a multi-syringe pump (PHD 200, Harvard Apparatus) at a flow rate of 8 $\mu$L/min/syringe (1 cc syringes). A Rheodyne valve (Model 9725) was used for flow switching. The column effluent combined with the make-up flow (10% 2 mM NH$_4$OAc buffer in acetonitrile) in the tee to provide a flow rate of 16 $\mu$L/min into the mass spectrometer.

Figure 5C:
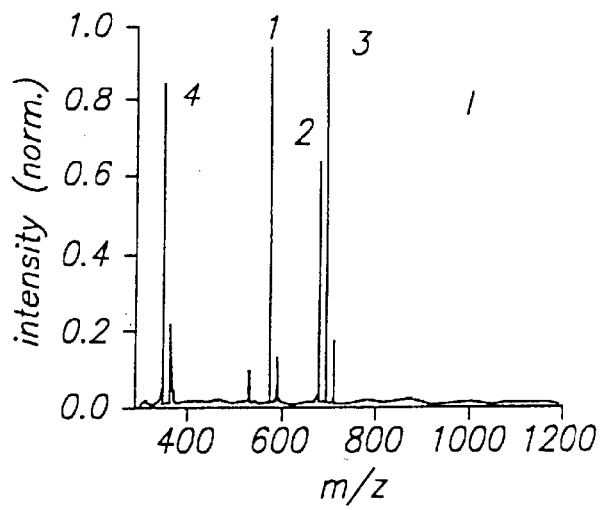
FIGS. 5C, 5D and 5E show mass spectra generated from time-slices of the TIC shown in FIG. 5A.
Figure 5D:
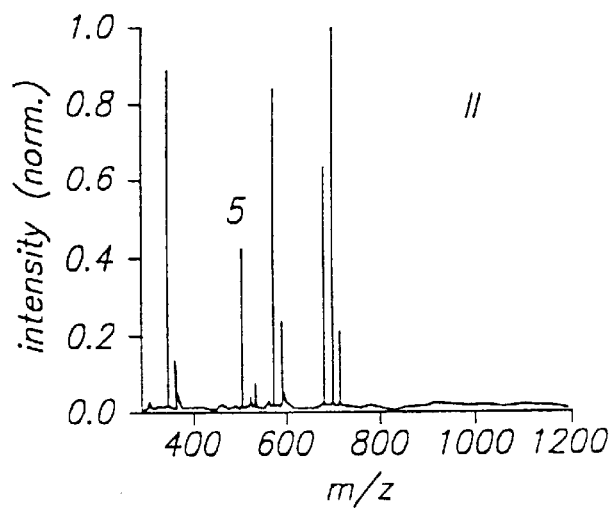
Figure 5E:
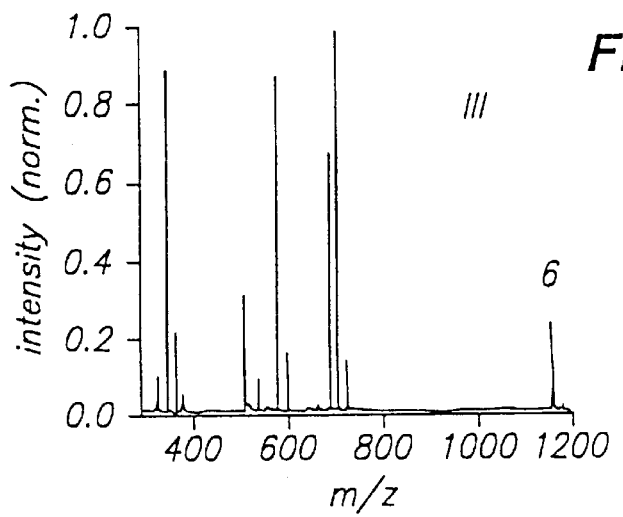

For the analysis of this mixture, the spectrometer was scanned from m/z 100–1500. Data was collected in scan mode with positive ion detection. A total ion chromatogram (TIC) was constructed from a 50 minute run time as shown in FIG. 5A. This represented the consumption of only 400 pmol of each oligosaccharide. Peaks at specific m/z values were then identified through the analysis of the mass spectra giving rise to the TIC and selected ion chromatograms for all six compounds were reconstructed from the TIC as shown in FIG. 5B. Compounds 1–3 break through the column simultaneously as indicated by the solid line. Mass spectra were then generated from time-slices of the TIC (at times I, II and III) as shown in FIGS. 5C, 5D and 5E. These mass spectra chart the progression of the various oligosaccharides through the column. A spectrum representing the onset of compound 4 is not shown.

As discussed above, ligands having no affinity for the target receptor break through at the void volume ($V_0$), while compounds having an affinity for the target receptor break through later, at volumes relating to their concentrations and $K_d$ values, according to the following equation:

$$V_x - V_0 = \frac{B_t}{[X]_0 + (K_d)_x}$$

where $B_t$ represents the dynamic binding capacity of the column; $[X]_0$ is the infusion concentration of the ligand in the compound library; $K_d$ is the dissociation constant for the ligand; $V_0$ is the void volume; and $V_x$ represents the volume at the mid-point of the front corresponding to the break through of the ligand.

Figure 6:
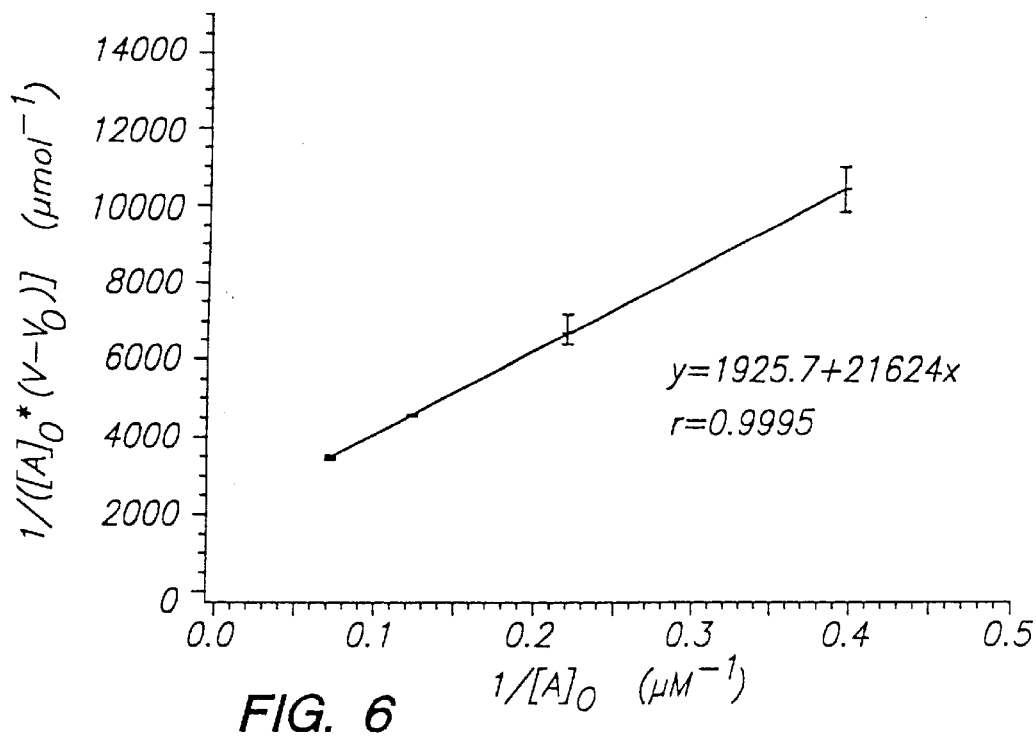
FIG. 6 shows a plot of $([A]_0(V-V_0))^{-1}$ versus $[A]_0^{-1}$ for $\alpha Gal(1\rightarrow 2)[\alpha Abe(1\rightarrow 3)]\alpha Man-OCH_3$.

In order to determine $B_t$, compound 5 was infused through the column at various concentrations and the corresponding $V-V_0$ values measured. A plot of $([A]_0(V-V_0))^{-1}$ versus $[A]_0^{-1}$ was generated, where A is compound 5, as shown in FIG. 6. The y-intercept indicated a $B_t$ of 520 pmol. Each antibody molecule contains two binding sites, therefore this corresponds to an active capacity of 260 pmol of protein (representing 93% of the total amount of protein bound). The x-intercept indicated a $K_d$ of 11.2 $\mu$M for compound 5, which compares favorably with the value determined by microcalorimetry as shown in Table 1.

Knowledge of the column capacity prior to the screening of a mixture allows for the determination of dissociation constants from a single frontal chromatogram. For compounds with $[X]<<(K_d)_x$, the $K_d$ can be determined simply from $B_t/(V-V_0)$. For example, compound 4 was shown to have a $K_d$ of 0.2 mM, as determined from the chromatogram of FIG. 5B. Compounds with low dissociation constants require either the knowledge of their concentration or the infusion of the mixture at higher dilution for the determination of $K_d$. The $K_d$ of compound 6, at a 1 $\mu$M concentration, was determined from the same chromatogram to be 1.5 $\mu$M.

The column was regenerated offline by washing with a large volume of binding buffer. The column used in this example was subjected to over 150 runs with no observable loss of activity or leaching of the antibody.

The results from this experiment are shown in Table 1.

TABLE 1

| No. | Oligosaccharide[1] | (MNa)$^+$ | $K_d^2$ Literature | $K_d^2$ FC/MS |
|---|---|---|---|---|
| 1 | αGalNAc(1→3)Gal-OGr | 576.3 | — | — |
| 2 | αGal(1→3)[αFuc(1→2)]βGal-OGr | 681.3 | — | — |
| 3 | αMan(1→3)[αMan(1→6)]-βMan-OGr | 697.3 | — | — |
| 4 | αAbe(1→3)αTal-OCH$_3$ | 347.0 | $1.9 \times 10^{-4}$ | $1.6 \times ^{-7}$ |
| 5 | αGal(1→2)[αAbe(1→3)]-αMan-OCH$_3$ | 509.2 | $6.3 \times 10^{-6}$ | $1.1 \times ^{-7}$ |
| 6 | αGlc(1→4)βGlc(1→4)-αGal(1→2)-[αAbe(1→3)]-αMan(1→3)αGlc(1→4)-βGlc-OCH$_3$ | 1157.4 | $8.8 \times 10^{-7}$ | $1.5 \times ^{-7}$ |

[1] Gr = O(CH$_2$)$_8$CO$_2$CH$_3$.
[2] $K_d$ = dissociation constant.

The results in Table 1 demonstrate that the affinity of various putative ligands in a compound library for a target receptor can be determined relative to other putative ligands in the library; and that the dissociation constant, $K_d$, for putative ligands and the target receptor can be determined. The results further demonstrate that there is an acceptable correlation between the literature $K_d$ values and those generated by FC-MS procedures.

Example 2

Screening of an Oligosaccharide Library Using FC-MS and an Indicator Compound

In this example, the use of an indicator compound to screen a compound library is demonstrated. The antibody used in this example was the same as that used in Example 1, i.e., a monoclonal antibody that recognizes the 3,6-dideoxy-D-galactose (abequose) epitope in *Salmonella paratyphi* B O-antigens. The column was also essentially the same as the column in Example 1 and it was prepared and operated as described therein.

In this experiment, three solutions were prepared. Solution A contained the following four oligosaccharide in 2 mM NH$_4$OAc: αGalNAc(1→3)βGal-OGr (compound 1); αGal (1→3)[αFuc(1→2)]βGal-OGr (compound 2); αMan(1→3) [αMan(1→6)]βMan-OGr (compound 3); αAbe(1→3)αTal-OCH$_3$ (compound 4), wherein Gr=O(CH$_2$)$_8$CO$_2$CH$_3$. Solution B contained αGal(1→2)[αAbe(1→3)]αMan-OCH$_3$ (compound 5) in 2 mM NH$_4$OAc; and Solution C contained compounds 1–5 in 2 mM NH$_4$OAc. In all solutions, compounds 1, 2 and 3 were present at 1 $\mu$M, compound 4 was present at 0.16 $\mu$M, and compound 5 was present at 15 $\mu$M. In this example, compound 4 was used as the indicator compound and compound 5 was used to represented a member of a compound library. The remaining compounds were used to determine $V_o$.

Solution A containing compounds 1–4 was infused into the column as described in Example 1. A quadrupole mass spectrometer was used to monitor the effluent. The mass spectrometer was operated in selected ion monitoring (SIM) mode, on the (M+Na)$^+$peak of each compound. FIG. 5A shows the selected ion chromatograms generated from an infusion of compounds 1–4 (i.e., Solution A). The breakthrough volume for compound 4 was 3.0±0.1 $\mu$L. The column was regenerated by flushing with the binding buffer (i.e., 2 mM NH$_4$OAc) for about 10 min. at which time essentially all traces of compound 4 were removed.

Figure 7A:
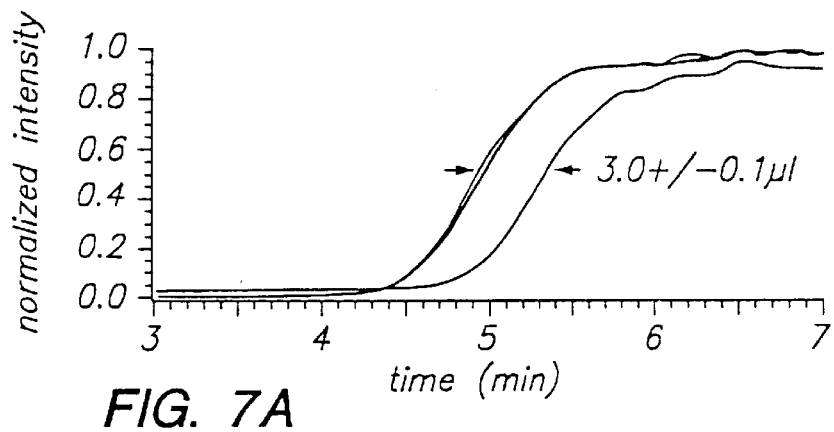
FIG. 7A shows a selected ion chromatogram from a FC-MS run using an indicator compound in the absence of a compound library.
Figure 7B:
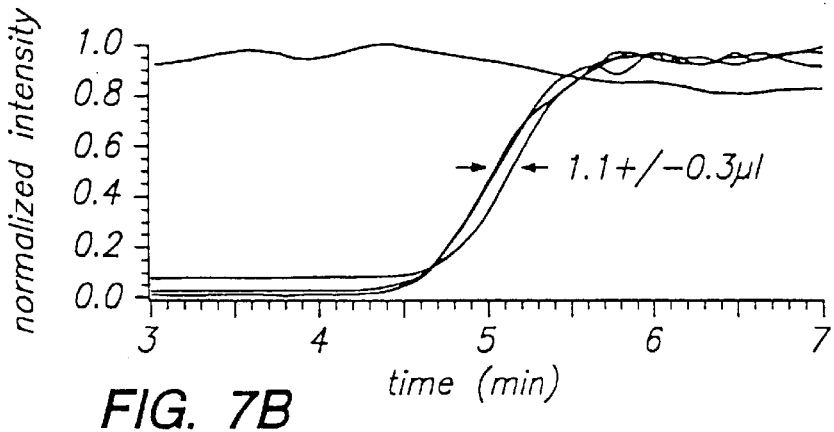
FIG. 7B shows a selected ion chromatogram from a FC-MS run using an indicator compound in the presence of a compound library.
Figure 8:
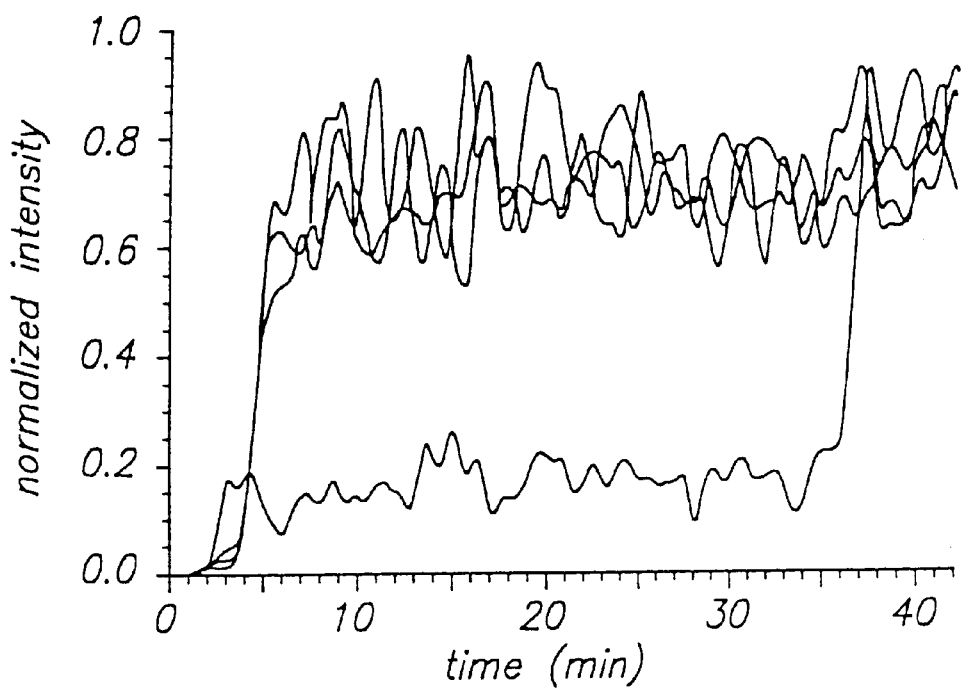
FIG. 8 shows a selected ion chromatogram from a FC-MS run using four representative oligosaccharides having varying affinity for cholera toxin B subunit.
Figure 9:
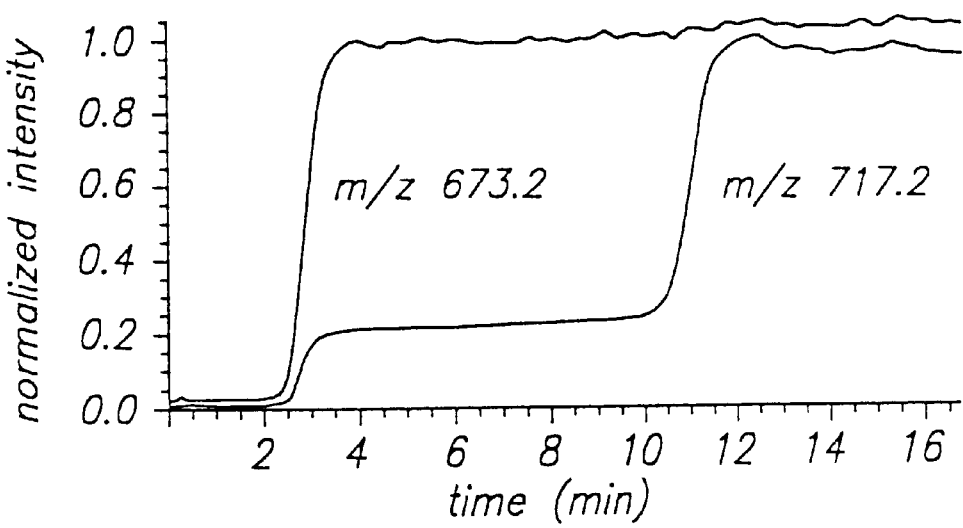
FIG. 9 shows a selected ion chromatogram from a FC-MS run using a synthetically prepared $GM_1$ analog.

Using the apparatus of FIG. 1, Solution B (compound 5) and Solution C (compounds 1–5) were loaded into separate syringes. Solution B was infused through the column until dynamic equilibrium for compound 5 was attained. At this point, the flow was switched to the syringe carrying Solution C, and the selected ion chromatograms of FIG. 7B were generated using the quadrupole mass spectrometer. As shown in FIG. 7B, pre-equilibration of the column with compound 5 leads to a measurable shift in the breakthrough volume of the indicator compound 4 (to 1.1±0.3 μl). This is consistent with the fact that compound 5 is a ligand having a $K_d$ for the antibody lower than that of the indicator compound 4 (see Table 1 above). Therefore, by simply monitoring the indicator compound, the fact that the representative library contained a compound with a higher affinity for the target receptor was readily apparent.

Note that while the indicator compound (compound 4) in this experiment was added to a solution of the representative library (compound 5), this will not always be necessary. In those situations where the library (Solution B) contains a strongly retained compound (i.e., low $K_d$, or off-rate), Solution A can be substituted for Solution C (i.e., the indicator does not need to be mixed with the library).

Example 3

Screening of an Oligosaccharide Library Using FC-MS

In this example, a compound library containing a mixture of four oligosaccharides was screened using frontal chromatography in combination with an electrospray mass spectrometer to determine the relative affinity of the oligosaccharides for cholera toxin B subunit.

The compound library consisted of the following four oligosaccharides: αGalNAc(1→3)βGal-OGr (compound 1); αGal(1→3)[αFuc(1→2)]βGal-OGr (compound 2); αMan (1→3)[αMan(1→6)]βMan-OGr (compound 3); and $GM_1$ oligosaccharide (compound 7, wherein Gr=$O(CH_2)_8CO_2CH_3$. Compound 7, which is the natural ligand for cholera toxin B subunit, was obtained using the procedures described in A. Schön et al., "Thermodynamics of Intersubunit Interactions in Cholera Toxin upon Binding to the Oligosaccharide Portion of Its Cell Surface Receptor, Ganglioside $G_{M1}$" Biochem. 1989, 28, 5019–5024, the disclosure of which is incorporated herein by reference in its entirety. Cholera toxin B subunit was obtained from LIST Biochemicals, Campbell, Calif.

A column was prepared from a 12 cm section of 0.01" (250 μm) i.d. PEEK tubing (column volume of about 6 μL). The column was packed with POROS 20 immobilized streptavidin particles (available from Perseptive Biosystems, Framingham, Mass.).

Cholera toxin B subunit (a pentameric protein) was biotinylated to provide about 1–2 biotins/monomer, as measured by MALDI. A dilute solution of this biotinylated protein (4 μM) was infused through the pre-packed column such that the total amount of cholera toxin B subunit bound was approximately 200 pmol after washing (as determined by UV quantitation).

A solution containing compounds 1–3 and 7 was prepared. All compounds were present at 2 μM, in 2 mM $NH_4OAc$ (pH 6.9). Using an apparatus similar to that shown in FIG. 1, the column was first equilibrated with the binding buffer (2 mM $NH_4OAc$). The solution containing compounds 1–3 and 7 was then infused through the column at 8 μL/min. The effluent was combined with a typical make-up flow (10% 2mM $NH_4OAc$ in acetonitrile) and passed into an electrospray single quadrupole mass spectrometer. Data was collected in scan mode, with negative ion detection.

A total ion chromatogram was generated, followed by reconstruction of selected ion chromatograms for each of compounds 1–3 and 7 as shown in FIG. 8. As illustrated in FIG. 8, compounds 1–3 broke through in the void volume of the system (~4 min×8 μL/min=32 μL) while compound 7 ($GM_1$ oligosaccharide) broke through at ~300 μL. Thus, $GM_1$ oligosaccharide ($K_d$≅100 nM) has a stronger affinity for cholera toxin B subunit than compounds 1–3 which have little or no affinity for cholera toxin B subunit.

A second mixture was then prepared in the binding buffer and analyzed by FC-MS in a similar fashion. This mixture contained a synthetically prepared $GM_1$ analogue, i.e., βGal (1→3)βGalNAc(1→)-$OCH_2CH_2O$-(←2)αNeu5Ac, (compound 8) in an impure form (i.e. containing unidentified intermediates and reaction byproducts). Compound 8 was prepared by the methods described in P. Fügedi et al, "A Novel Promoter for the Efficient Construction of 1,2-trans Linkages in Glycoside Synthesis, Using Thioglycosides as Glycosyl Donors" *Carbohydr. Res.* 1986, 149, C9–C12; A. Marra et al., Stereoselective Synthesis of 2-Thioglycosides of N-Acetylneuraminic Acid", *Carbohydr. Res.* 1989, 187, 35–42; and L. Lay et al., "Synthesis of the Propyl Glycoside of the Trisaccharide α-L-Fucp-(1→2)-β-D-Galp-(1→3)-β-D-GalpNAc. Components of a Tumor Antigen Recognized by the Antibody Mbr1" *Helv. Chim. Acta.* 1994, 77, 509–514; the disclosures of which are incorporated herein by reference in their entirety. The mixture was infused through the column, and the mass spectrometer was set to operate in selected ion monitoring mode, on negative ions representative of compounds 3 and 8. Selected ion chromatograms were generated for these ions as shown in FIG. 9. FIG. 9 shows that compound 3 broke through in the void volume (m/z 673.2). A more complex pattern was observed for the ions with a mass/charge of 717.2 u. A certain fraction of these ions also broke through in the void volume (~25%), while the remaining 75% broke through significantly later (at about 11 min). This two-front profile indicates an isobaric impurity exists at the 25% level, which does not bind to cholera toxin B subunit. Thus, FC-MS is able to ascertain the presence of isobaric, non-binding impurities. Reasonably accurate quantitation of these impurities can also be achieved.

From the foregoing description, various modifications and changes in the composition and method will occur to those skilled in the art. All such modifications coming within the scope of the appended claims are intended to be included therein.

What is claimed is:

1. An apparatus for screening a compound library to determine the relative or absolute affinity of a plurality of putative ligands to a target receptor, which apparatus comprises:

(a) a column comprising a target receptor optionally attached to a solid phase support and having a inflow end and an outflow end, wherein said column is capable of having a compound library comprising a plurality of putative ligands continuously applied thereto under frontal chromatography conditions whereby the target receptor is continuously contacted with the compound library to produce an effluent from the outflow end of the column;

(b) a first reservoir connected to the inflow end of said column for continuously applying the compound library to the column;

(c) a mass spectrometer connected to the outflow end of said column for continuously or intermittently analyzing the effluent from the column.

2. The apparatus of claim 1, wherein said apparatus further comprises:
(d) a second reservoir connected to the inflow end of the column for applying either (i) a mixture comprising the compound library and one or more indicator compounds, (ii) one or more indicator compounds, or (iii) a buffer solution to the column.

3. The apparatus of claim 1, wherein said apparatus further comprises:
(e) a third reservoir connected to the outflow end of the column for supplying a supplemental diluent to the effluent before analysis by the mass spectrometer.

4. The apparatus of claim 1, wherein the column has an internal diameter ranging from about 10 $\mu$m to about 4.6 mm.

5. The apparatus of claim 4, wherein the column has an internal diameter of from about 100 $\mu$m to about 250 $\mu$m.

6. The apparatus of claim 1, wherein the column has a length of from about 1 cm to about 30 cm.

7. The apparatus of claim 1, wherein the column has a length of from about 2 cm to about 20 cm.

8. The apparatus of claim 1, wherein the target receptor is selected from the group consisting of proteins, glycoproteins, glycosaminoglycans, proteoglycans, integrins, enzymes, lectins, selecting, cell-adhesion molecules, toxins, bacterial pili, transport proteins, receptors involved in signal transduction or hormone-binding, hormones, antibodies, major histocompatability complexes, immunoglobulin superfamilies, cadherins, DNA or DNA fragments, RNA and RNA fragments, whole cells, tissues, bacteria, fungi, viruses, parasites, preons, and synthetic analogs or derivatives thereof.

9. The apparatus of claim 1, wherein the target receptor is bound to a solid phase support.

10. The apparatus of claim 9, wherein the target receptor is covalently bound to the solid phase support or bound via biotin-avidin or biotin-streptavidin binding.

11. The apparatus of claim 9, wherein the solid phase support is selected from the group consisting of resin beads, glass beads, silica chips, silica capillaries and agarose.

12. The apparatus of claim 1, wherein the column contains from about 1 pmol to about 10 nmol of target receptor active sites.

13. The apparatus of claim 1, wherein the mass spectrometer is an electrospray mass spectrometer.

* * * * *